US011999729B2

(12) United States Patent
Qi et al.

(10) Patent No.: US 11,999,729 B2
(45) Date of Patent: Jun. 4, 2024

(54) SMALL MOLECULE INHIBITION OF TRANSCRIPTION FACTOR SALL4 AND USES THEREOF

(71) Applicants: DANA-FARBER CANCER INSTITUTE, INC., Boston, MA (US); THE BRIGHAM AND WOMEN'S HOSPITAL, INC., Boston, MA (US)

(72) Inventors: Jun Qi, Sharon, MA (US); Anthony Varca, Wethersfield, CT (US); Li Chai, Sudbury, MA (US)

(73) Assignees: DANA-FARBER CANCER INSTITUTE, INC., Boston, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 17/978,591

(22) Filed: Nov. 1, 2022

(65) Prior Publication Data

US 2023/0115483 A1  Apr. 13, 2023

Related U.S. Application Data

(62) Division of application No. 16/753,536, filed as application No. PCT/US2018/054317 on Oct. 4, 2018, now Pat. No. 11,530,209.

(60) Provisional application No. 62/567,939, filed on Oct. 4, 2017.

(51) Int. Cl.
*C07D 471/04* (2006.01)
*C07D 487/04* (2006.01)
*C07D 519/00* (2006.01)

(52) U.S. Cl.
CPC ......... *C07D 471/04* (2013.01); *C07D 487/04* (2013.01); *C07D 519/00* (2013.01)

(58) Field of Classification Search
CPC .................................................. C07D 471/04
USPC ....................................................... 514/249
See application file for complete search history.

(56) References Cited

U.S. PATENT DOCUMENTS

| | | | |
|---|---|---|---|
| 6,638,933 B2 | 10/2003 | Gerlach et al. | |
| 6,699,873 B1 | 3/2004 | Maguire et al. | |
| 8,227,603 B2 | 7/2012 | Russell et al. | |
| 8,557,801 B2 * | 10/2013 | Chatterjee | C07F 5/022 514/233.2 |
| 9,365,851 B2 | 6/2016 | Chai et al. | |
| 9,975,896 B2 * | 5/2018 | Marineau | A61P 29/00 |
| 11,731,967 B2 * | 8/2023 | Qi | C07D 471/04 514/233.2 |
| 2003/0144518 A1 | 7/2003 | Chen | |
| 2004/0023972 A1 | 2/2004 | Sundermann et al. | |
| 2004/0058938 A1 * | 3/2004 | Cullmann | C07D 471/04 514/249 |
| 2020/0317664 A1 | 10/2020 | Qi et al. | |

FOREIGN PATENT DOCUMENTS

| | | | |
|---|---|---|---|
| KR | 20110097448 A | | 8/2011 |
| WO | 2001027119 | * | 4/2001 |
| WO | 2006131003 A1 | | 12/2006 |
| WO | 2007076055 | * | 7/2007 |
| WO | 2008016648 A2 | | 2/2008 |
| WO | 2008068392 A1 | | 6/2008 |
| WO | 2014021383 A1 | | 2/2014 |
| WO | 2015013635 A2 | | 1/2015 |
| WO | 2015143652 A1 | | 10/2015 |
| WO | 2017190032 A2 | | 11/2017 |
| WO | 2018200988 A1 | | 11/2018 |

OTHER PUBLICATIONS

Guchhait et al., Journal of Organic Chemistry (2012), 77(18), 8321-8328.*
Varma et al., Journal of Heterocyclic Chemistry (1999), 36(6), 1565-1571.*
Varma et al., Tetrahedron Letters (1999), 40(43), 7665-7669.*
Bienayme et al., Angewandte Chemie, International Edition (1998), 37(16), 2234-2237.*
Groebke et al., Synlett (1998), (6), 661-663.*
Blackburn et al., Tetrahedron Letters (1998), 39(22), 3635-3638.*
Akritopoulou-Zanze et al., "Scaffold oriented synthesis part 4: Design, synthesis and biological evaluation of novel 5-substituted indazoles as potent and selective kinase inhibitors employing heterocycle forming and multicomponent reactions," Bioorg Med Chem Lett, 21:1480-1483 (2011).
Burchak et al., "Combinatorial Discovery of Fluorescent Pharmacophores by Multicomponent Reactions in Droplet Arrays," Journal of the American Chemical Society, vol. 133(26), pp. 10058-10061 (2011).
Extended European Search Report for EP Application No. EP 18864364.7 dated Feb. 17, 2021 (8 pgs.).
International Search Report and Written Opinion for International Application No. PCT/US18/54317 dated Jan. 24, 2019 (9 pgs.).
PubChem Compound Database, PubChem CID: 9816660. <Retrieved from Internet: https://pubchem.ncbi.nlm.nih.gov/compound/9816660>.
Reutlinger et al., "Chemically Advanced Template Search (CATS) for Scaffold-Hopping and Prospective Target Prediction for 'Orphan' Molecules," Molecular Informatics, vol. 32(2), pp. 133-138 (2013).
Reutlinger et al., "Combining On-Chip Synthesis of a Focused Combinatorial Library with Computational Target Prediction Reveals Imidazopyridine GPCR Ligands," Angewandte Chemie, International Edition, vol. 53(2), pp. 582-585 (2014).
Shukla et al., "Antibacterial activities of Groebke-Blackburn-Bienayme-derived imidazo[1,2-α]pyridin-3-amines," Bioorg. Med. Chem. 20:5850-5863 (2012).

(Continued)

*Primary Examiner* — Niloofar Rahmani
(74) *Attorney, Agent, or Firm* — BURNS & LEVINSON, LLP; Daniel W. Clarke; Shawn P. Foley

(57) ABSTRACT

Provided herein are compounds that interrupt the function of SALL4. Also described are pharmaceutical compositions and medical uses of these compounds.

22 Claims, No Drawings

(56) References Cited

OTHER PUBLICATIONS

Jones, B., SALL4—A Cancer Marker and Target, Nat. Rev. Clin. Oncol., 2013, vol. 10, pp. 426.
Li et al., SALL4 is a new target in endometrial cancer, Oncogene, 2015, vol. 34, No. 1, pp. 63-72.
Ma et al., SALL4, a novel oncogene, is constitutively expressed in human acute myeloid leukemia (AML) and induces AML in transgenic mice, Blood, 2006, vol. 108, No. 8, pp. 2726-2735.
Oikawa et al., SALL4, a Stem Cell Biomarker in Liver Cancers, Hepatology, 2013, vol. 57, No. 4, pp. 1469-1483.

\* cited by examiner

SMALL MOLECULE INHIBITION OF TRANSCRIPTION FACTOR SALL4 AND USES THEREOF

RELATED APPLICATIONS

This application is a divisional of U.S. application Ser. No. 16/753,536, filed on Apr. 3, 2020, which is the U.S. National Stage application, filed under 35 U.S.C. § 371, of International Patent Application No. PCT/US2018/54317, filed on Oct. 4, 2018, which claims the benefit of priority under 35 U.S.C. § 119(e) to U.S. Provisional Patent Application Ser. No. 62/567,939, filed on Oct. 4, 2017, each of which is incorporated herein by reference in its entirety.

BACKGROUND

The embryonic stem cell gene SALL4 encodes a zinc finger transcription factor. Its expression is down-regulated during development, and absent in most adult tissues, but aberrantly re-expressed in cancer cells, including most AMLs. SALL4 is enriched in a "side-population (SP)" of the tumor cells. The SP is implicated in drug resistance and cancer initiation, and is used to isolate the cancer initiation cells (CICs). SALL4 expression is correlated with worse prognosis in AML patients as well. Knocking down the SALL4 gene by shRNA in leukemia leads to cell death and growth inhibition both in vitro and in vivo. However, targeting transcription factor DNA binding ability and direct inhibition of SALL4 remain challenging, as there are no reported SALL4 inhibitors.

Thus, there is a continuing need for pharmacologic agents that interrupt the function of SALL4 and that can be used to manipulate SALL4 in therapeutic or experimental applications.

SUMMARY OF INVENTION

In one aspect, the invention relates to compounds having the structure of Formula I or a pharmaceutically acceptable salt thereof:

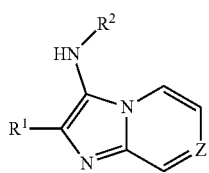

Formula I wherein $R^1$, $R^2$, and Z are defined herein.

In another aspect, the invention relates to pharmaceutical compositions of a compound of Formula I and a pharmaceutically acceptable carrier.

The invention also relates to methods of treating or preventing a disease or condition comprising administering a compound or composition of the invention. In certain embodiments, the disease is cancer. The invention further relates to methods of inhibiting proliferation of a cancer cell, comprising contacting a cancer cell with a compound or composition of the invention.

DETAILED DESCRIPTION OF THE INVENTION

In certain aspects, the invention provides various novel compounds, and pharmaceutical compositions thereof. In particular, such compounds are useful as SALL4 inhibitors, and thus can be used to treat or prevent a disease or condition (e.g., cancer).

I. Compounds

In certain embodiments, the invention relates to compounds having the structure of Formula I, or a pharmaceutically acceptable salt thereof:

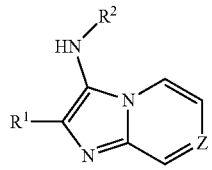

Formula I wherein

Z is N or $CR^3$;

$R^1$ is optionally substituted alkyl, cycloalkyl, heterocyclyl, aryl, or heteroaryl;

$R^2$ is optionally substituted alkyl, cycloalkyl, heterocyclyl, aryl, or heteroaryl; and $R^3$ is H or optionally substituted alkyl, carboxy or ester.

In certain embodiments, is N. In certain other embodiments, Z is $CR^3$. In certain embodiments, $R^3$ is H. In certain other embodiments, $R^3$ is ester (e.g., 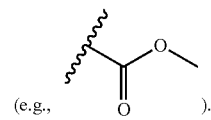 ).

In certain embodiments, $R^1$ is optionally substituted aryl (e.g., phenyl). In some embodiments, the aryl or phenyl is substituted with one more groups selected from halo, hydroxyl, boronic acid, cyano, optionally substituted alkyl, optionally substituted alkoxy, carboxy, amino, ester, and optionally substituted aryl. For example, in certain embodiments, $R^1$ is selected from

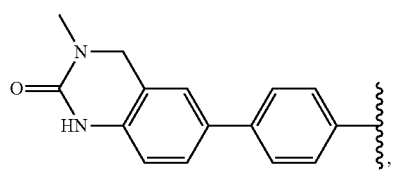

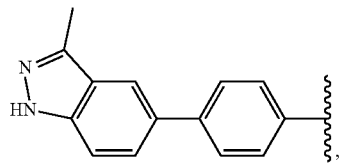

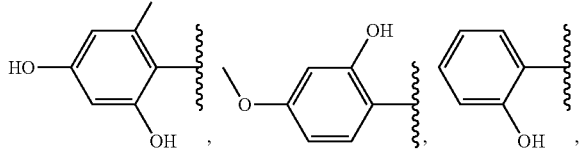

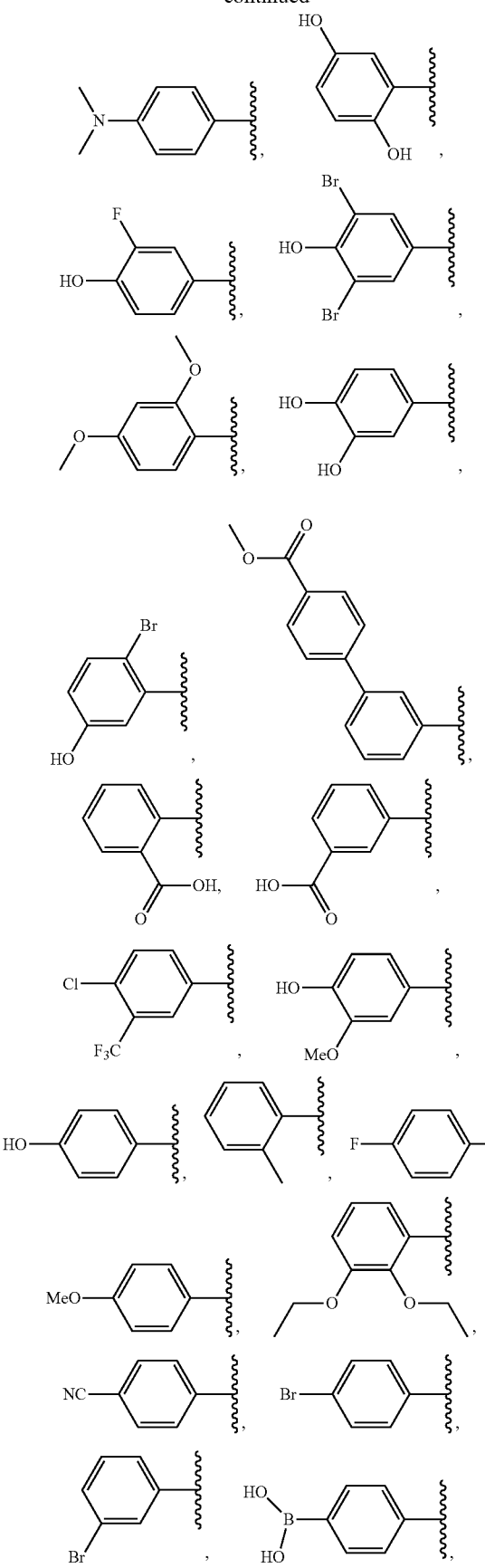
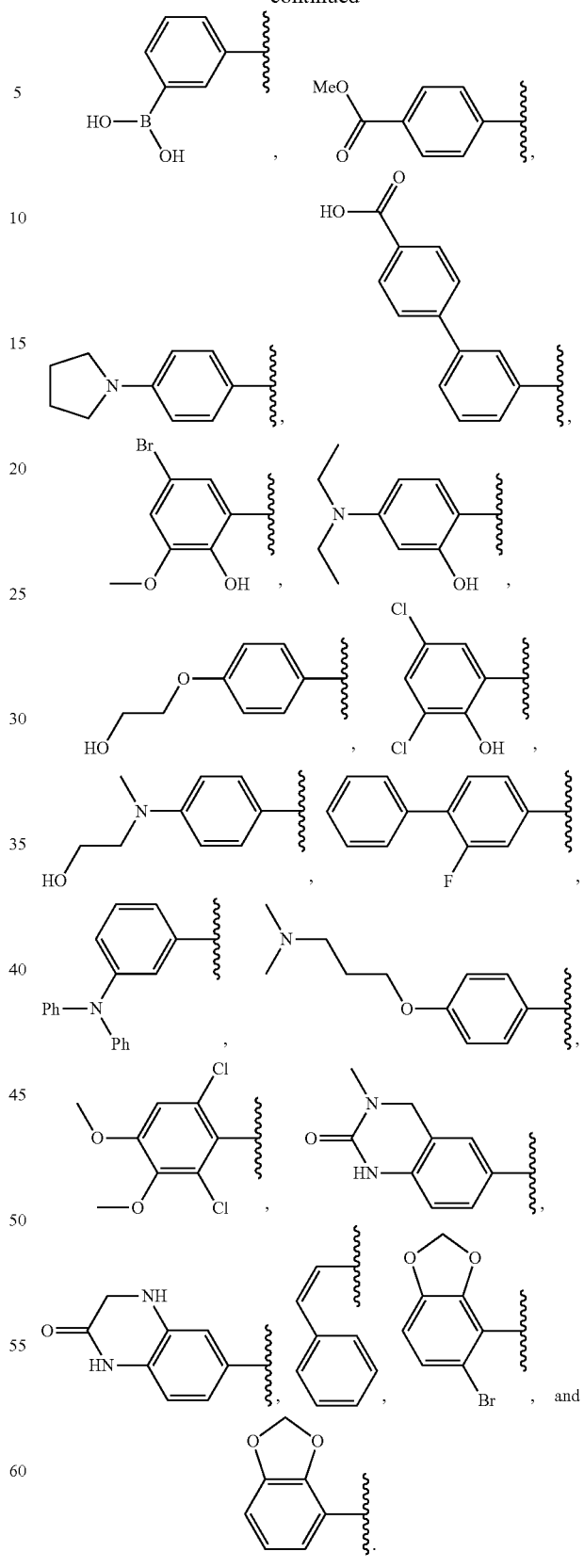
In certain embodiments, R[1] is selected from optionally substituted napthalenyl. In some embodiments, the napthalenyl is substituted with one or more groups selected from hydroxyl and nitro. For example, in certain embodiments, R¹ is selected from

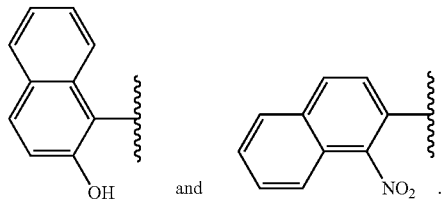 [SMILES: *c1c(O)ccc2ccccc12 ; *c1ccc2ccccc2c1[N+](=O)[O-]]

In certain embodiments, R¹ is optionally substituted alkyl, cycloalkyl, or heterocyclyl.

In certain embodiments, the alkyl is substituted with one or more groups selected from hydroxyl, alkoxy, optionally substituted alkyl, optionally substituted cycloalkyl, and optionally substituted aryl. For example, in certain embodiments, R¹ is selected from

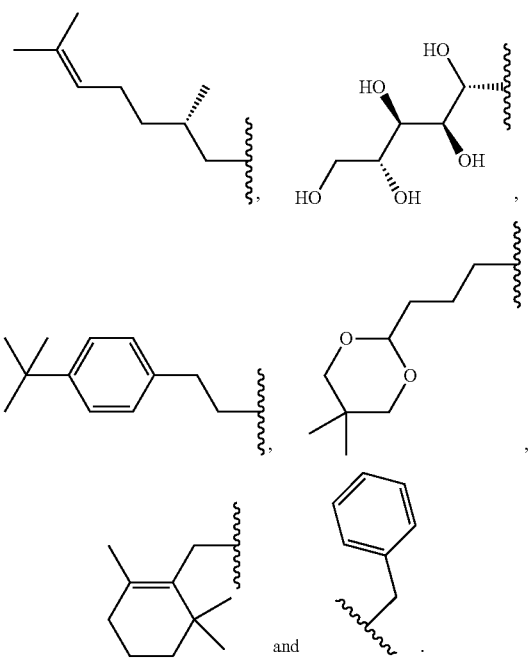

In certain embodiments, cycloalkyl comprises 3 to 8 carbon atoms. In certain embodiments, heterocyclyl comprises a nitrogen atom. For example, in certain embodiments, R¹ is selected from

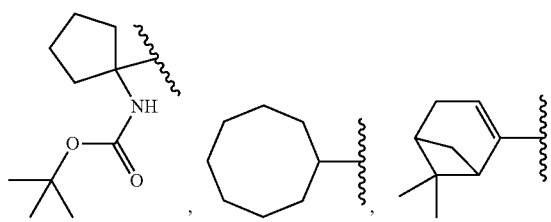

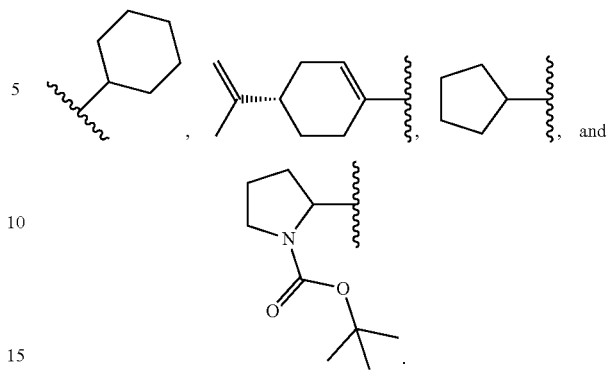

In certain embodiments, the optionally substituted heteroaryl is selected from oxazolyl, pyrazolyl, imidazolyl, indolyl, benzoisoxazolyl, indazolyl, azaindolyl, benzothiazolyl, thiazolyl, thiophenyl, furanyl, pyridinyl, pyrimidinyl, pyrrolyl, quinolinyl, and carbazolyl.

In certain embodiments, the heteroaryl is substituted with one or more groups selected from halo, oxy, nitro, sulfonate, and optionally substituted alkyl.

For example, in certain embodiments, R¹ is selected from

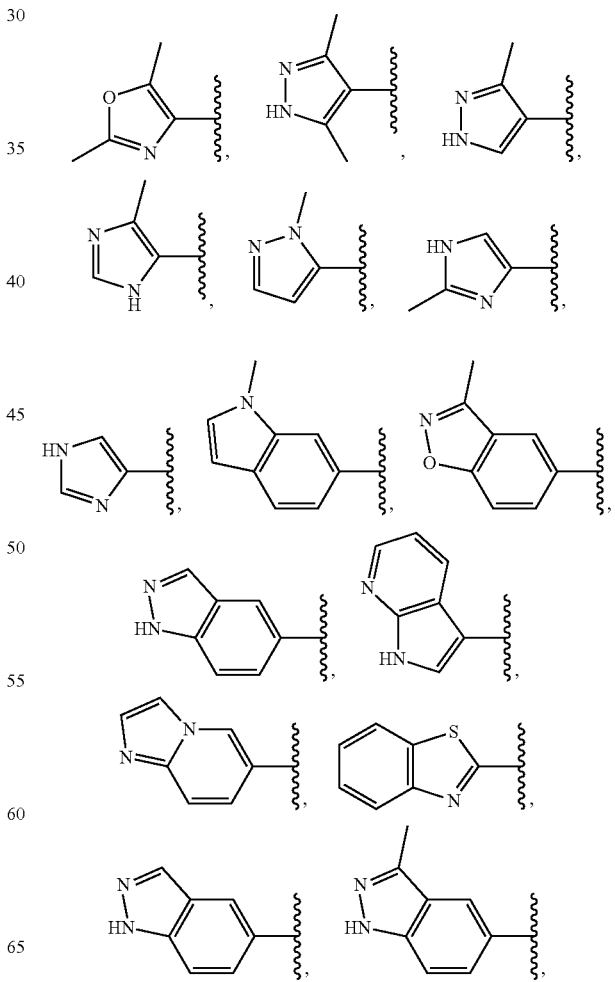

-continued

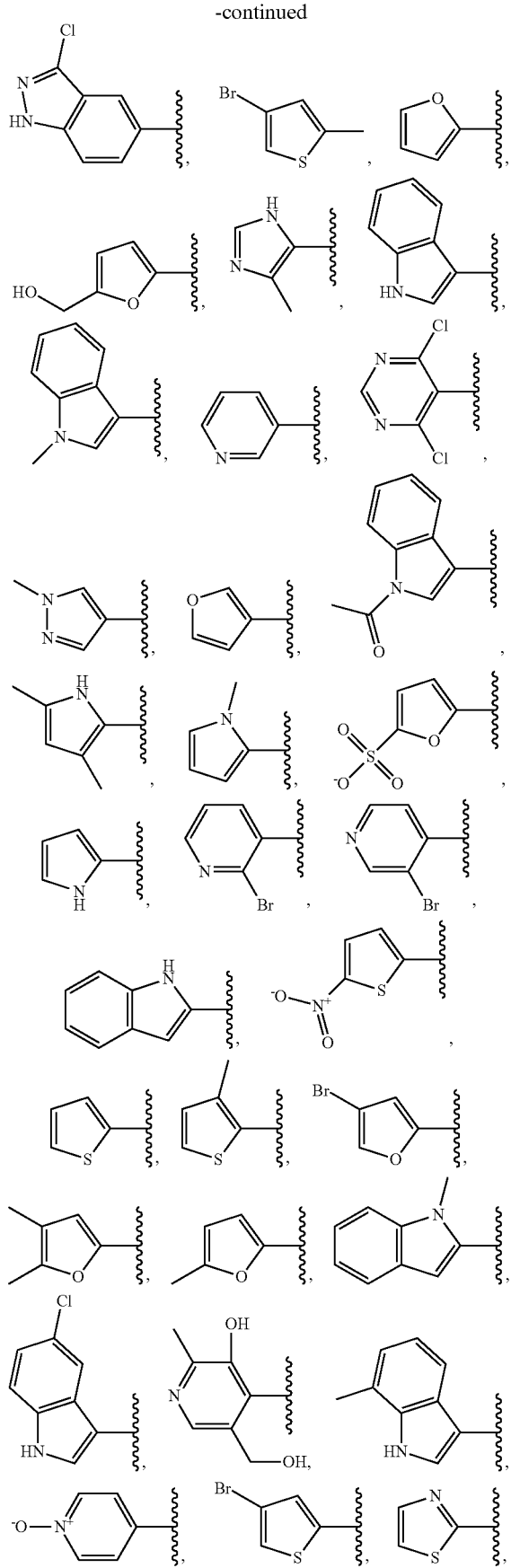

-continued

In certain embodiments, R² is optionally substituted alkyl, cycloalkyl, or aryl. In certain embodiments, alkyl is substituted with alkoxy, amino or optionally substituted aryl. For example, in certain embodiments, R² is selected from In certain embodiments, cycloalkyl comprises 3 to 6 carbon atoms. For example, in certain embodiments, R² is selected from In certain embodiments, wherein R² is optionally substituted aryl (e.g., phenyl). In certain embodiments, phenyl is substituted with one more groups selected from halo, hydroxyl, cyano, optionally substituted alkyl, optionally substituted alkoxy, carboxy, and ester. For example, in certain embodiments, R² is selected from

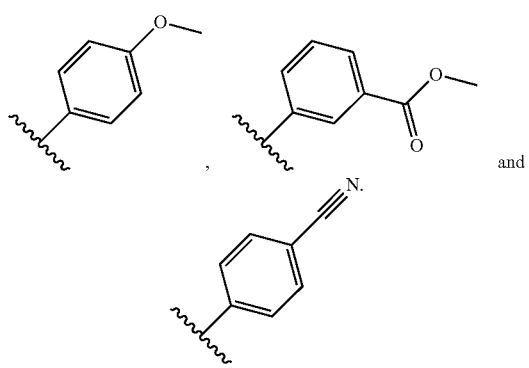

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, as will be described in detail below, the present invention relates to methods of treating or preventing a disease or condition with a compound of Formula I, or a pharmaceutically acceptable salt thereof. In certain embodiments, the therapeutic preparation may be enriched to provide predominantly one enantiomer of a compound of one of Formula I. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound of one of Formula I. A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient in the treatment of a disease or condition, comprising an effective amount of any compound of one of Formula I, and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Exemplary compounds of the invention are depicted in Tables 1, 2, 3, and 4. The compounds of Tables 1, 2, 3, and 4 are understood to encompass both the free base and the conjugate acid. For example, the compounds in Tables 1, 2, 3, and 4 may be depicted as complexes or salts with trifluoroacetic acid or hydrochloric acid, but the compounds in their corresponding free base forms or as salts with other acids are equally within the scope of the invention. Compounds may be isolated in either the free base form, as a salt (e.g., a hydrochloride salt) or in both forms. In the chemical structures shown below, standard chemical abbreviations are sometimes used.

TABLE 1

Compounds of Library 1

| Compound | |
|---|---|
| | B2 |
| | B3 |
| | C2 |
| | C3 |
| | D2 |

TABLE 1-continued
Compounds of Library 1
| Compound | |
|---|---|
| 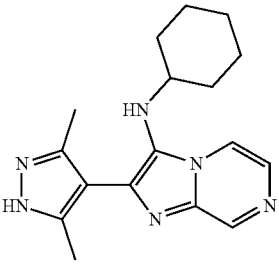 [SMILES: Cc1n[nH]c(C)c1-c1nc2cnccn2c1NC1CCCCC1] | D3 |
| 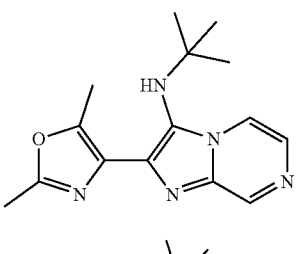 | E2 |
| 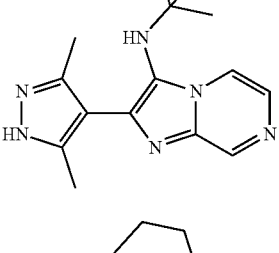 | E3 |
| 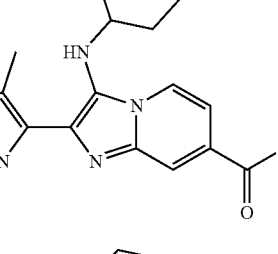 | F2 |
| 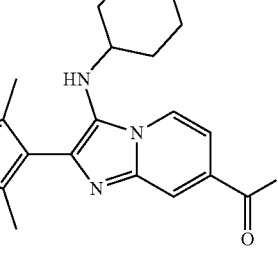 | F3 |
| 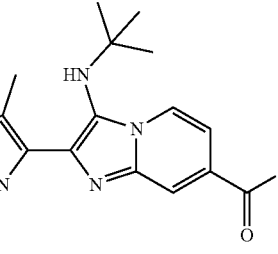 | G2 |
| 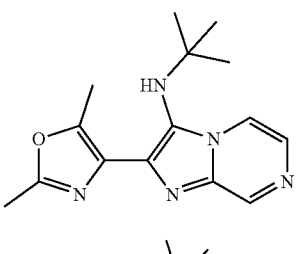 | G3 |
| 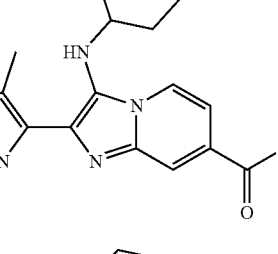 | B4 |
| 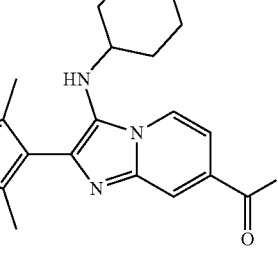 | B5 |
| 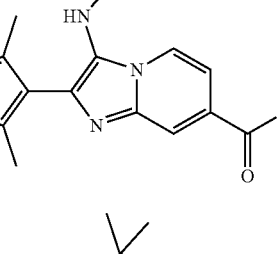 | C4 |
| 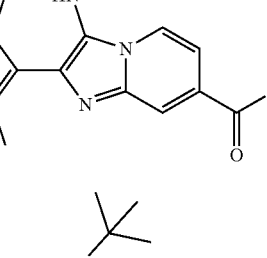 | C5 |
| 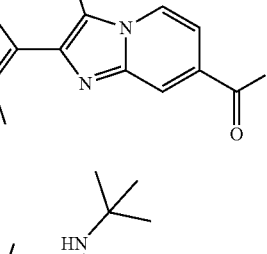 | D4 |

TABLE 1-continued
Compounds of Library 1
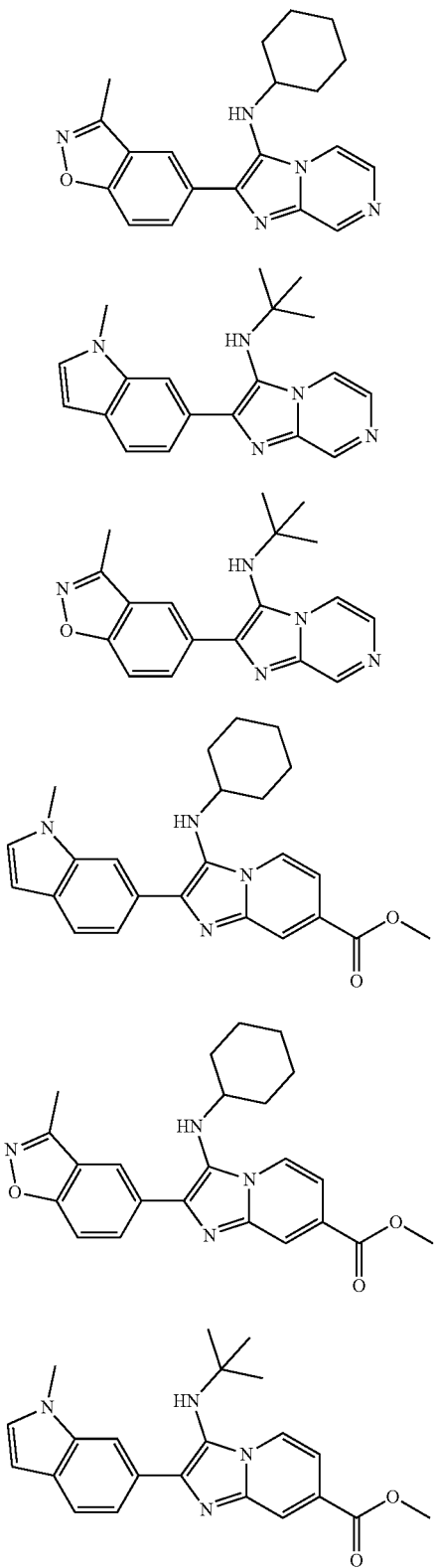
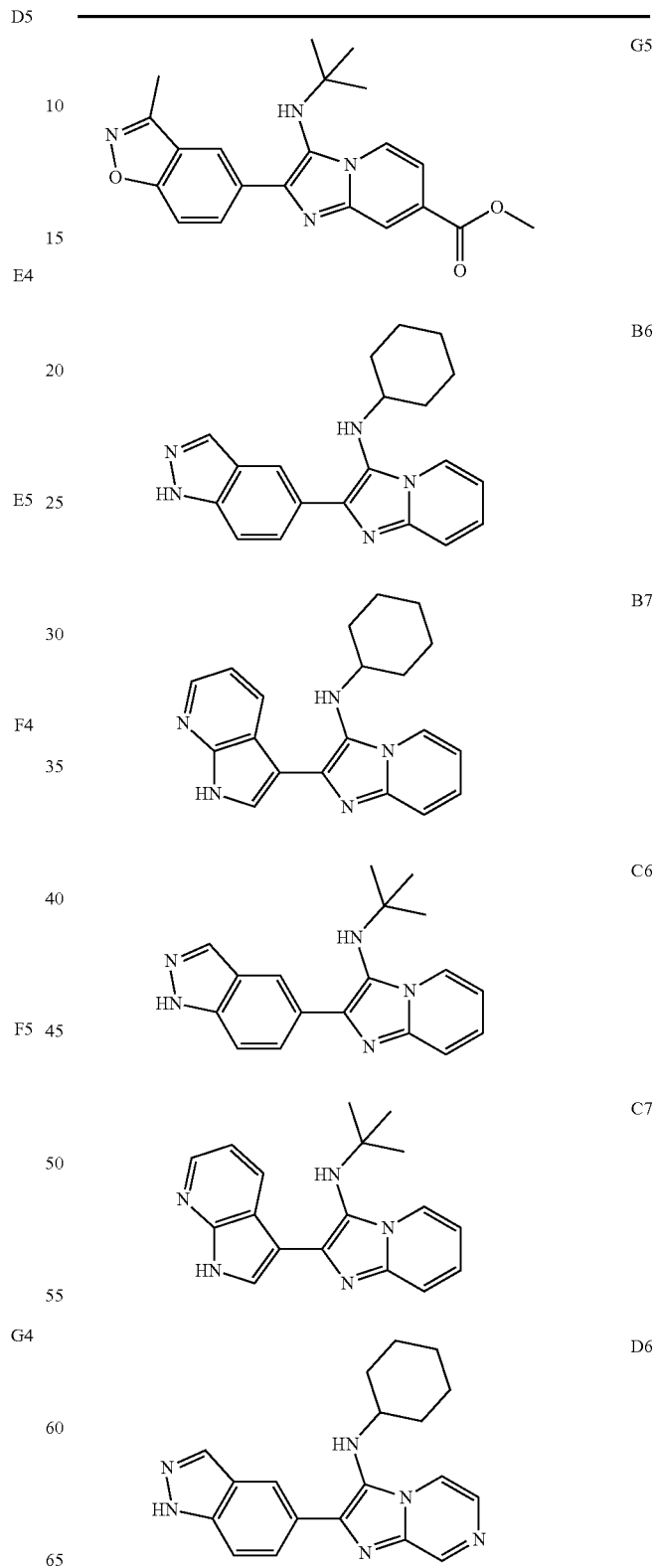

TABLE 1-continued

Compounds of Library 1

| Compound | |
|---|---|
| D7 | G7 |
| E6 | B8 |
| E7 | B9 |
| F6 | C8 |
| F7 | C9 |
| G6 | D8 |

TABLE 1-continued
Compounds of Library 1
| Compound |
|---|
| D9 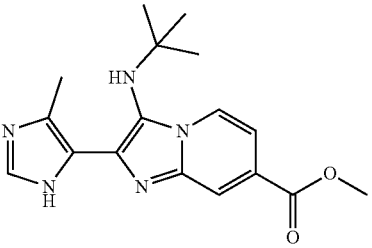 |
| E8 |
| E9 |
| F8 |
| F9 |
| G8 |
TABLE 1-continued
Compounds of Library 1
| Compound |
|---|
| G9 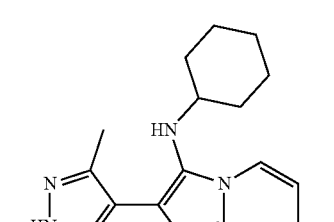 |
| B10 |
| B11 |
| C10 |
| C11 |
| D10 |

TABLE 1-continued
Compounds of Library 1
| Compound |
|---|
| D11 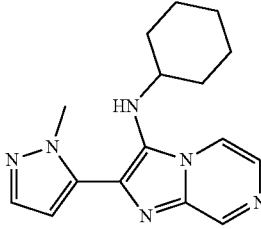 |
| E10 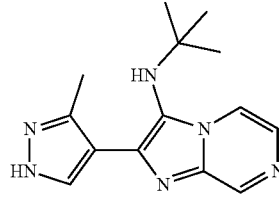 |
| E11 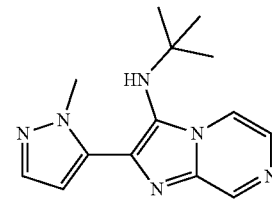 |
| F10 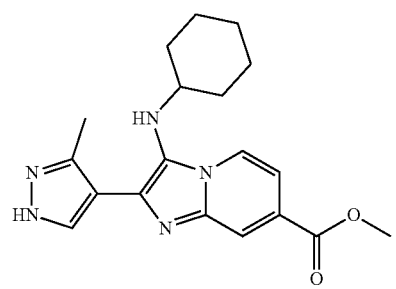 |
| F11 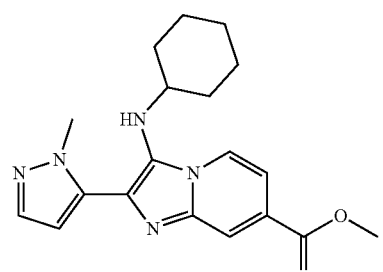 |
| G10 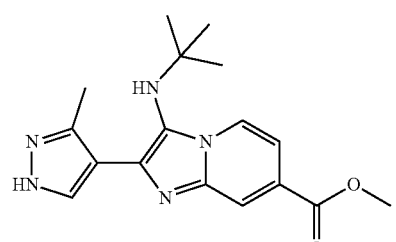 |
| G11 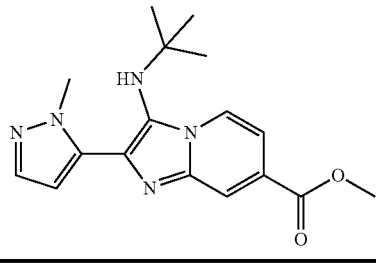 |
TABLE 2
Exemplary of Library 2
| Compound |
|---|
| B2 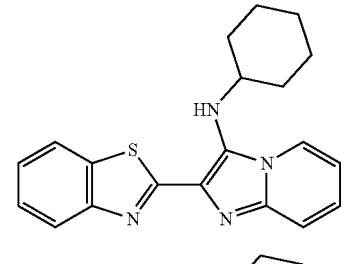 |
| B3 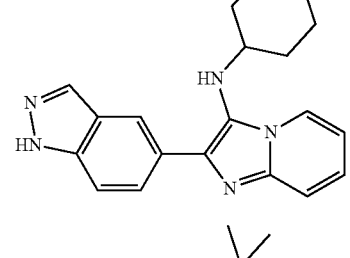 |
| C2 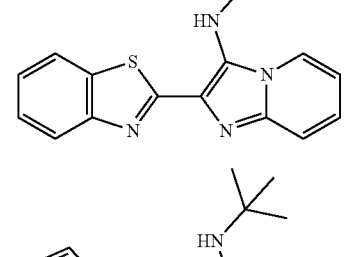 |
| C3 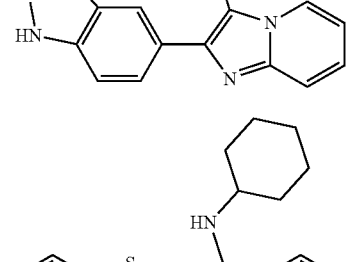 |
| D2 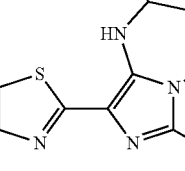 |

TABLE 2-continued

Exemplary of Library 2

Compound

TABLE 2-continued

Exemplary of Library 2

| Compound | |
|---|---|
| D5 | (structure) |
| E4 | (structure) |
| E5 | (structure) |
| F4 | (structure) |
| F5 | (structure) |
| G4 | (structure) |
| G5 | (structure) |
| B6 | (structure) |
| B7 | (structure) |
| C6 | (structure) |
| C7 | (structure) |
| D6 | (structure) |

TABLE 2-continued

Exemplary of Library 2

Compound

TABLE 2-continued

Exemplary of Library 2

| Compound | |
|---|---|
| D9 | (structure) |
| E8 | (structure) |
| E9 | (structure) |
| F8 | (structure) |
| F9 | (structure) |
| G8 | (structure) |
| G9 | (structure) |
| B10 | (structure) |
| B11 | (structure) |
| C10 | (structure) |
| C11 | (structure) |
| D10 | (structure) |

TABLE 2-continued
Exemplary of Library 2
| Compound | |
|---|---|
| 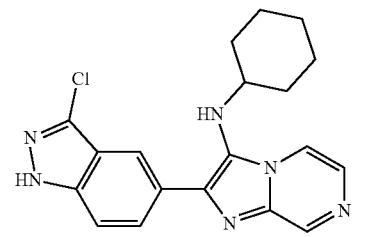 [SMILES: Clc1n[nH]c2ccc(-c3nc4cnccn4c3NC3CCCCC3)cc12] | D11 |
| 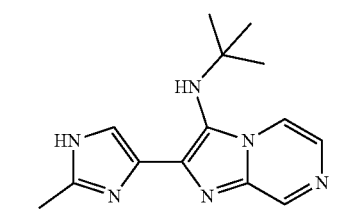 [SMILES: Cc1nc(-c2nc3cnccn3c2NC(C)(C)C)c[nH]1] | E10 |
| 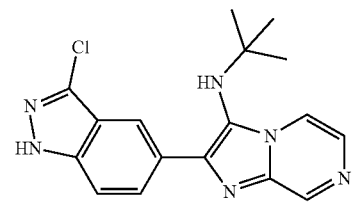 [SMILES: CC(C)(C)Nc1c(-c2ccc3[nH]nc(Cl)c3c2)nc2cnccn12] | E11 |
| 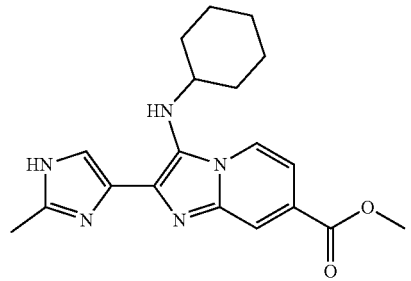 | F10 |
| 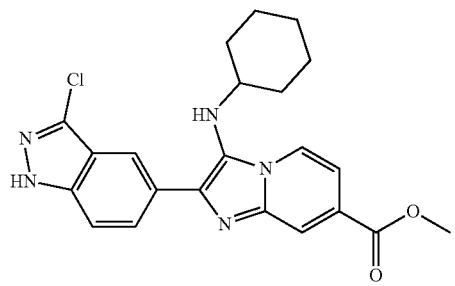 [SMILES: COC(=O)c1ccn2c(NC3CCCCC3)c(-c3ccc4[nH]nc(Cl)c4c3)nc2c1] | F11 |
| 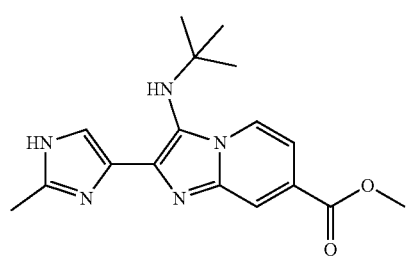 | G10 |
TABLE 2-continued
Exemplary of Library 2
| Compound | |
|---|---|
| 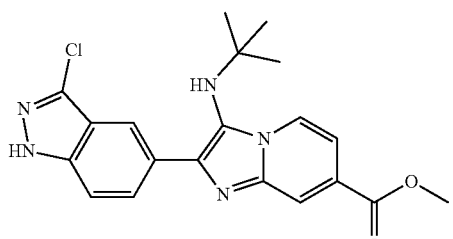 | G11 |
TABLE 3
Compounds of Library 3
| Compound | |
|---|---|
| DMSO | A1 |
| | A2 |
| 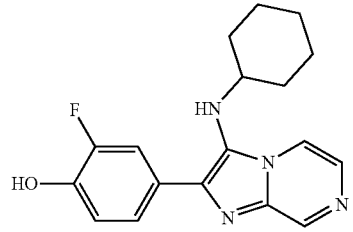 | |
| 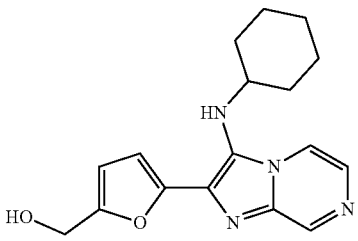 | B1 |
| 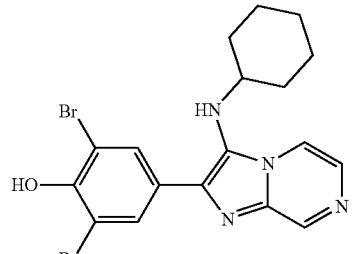 | B2 |
| 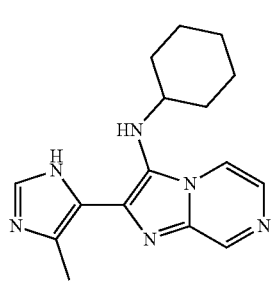 | C1 |

TABLE 3-continued

Compounds of Library 3

| Compound | |
|---|---|
| C2 | (structure: cyclohexyl-HN-imidazopyrazine with N-methylpyrazole) |
| D1 | (structure: cyclohexyl-HN-imidazopyrazine with 2,5-dihydroxyphenyl) |
| D2 | (structure: cyclohexyl-HN-imidazopyrazine with furan-3-yl) |
| E1 | (structure: cyclohexyl-HN-imidazopyrazine with indol-3-yl) |
| E2 | (structure: cyclohexyl-HN-imidazopyrazine with N-acetyl-indol-3-yl) |
| F1 | (structure: cyclohexyl-HN-imidazopyrazine with pyridin-3-yl) |
| F2 | (structure: cyclohexyl-HN-imidazopyrazine with 2,4-dimethoxyphenyl) |
| G1 | (structure: cyclohexyl-HN-imidazopyrazine with styryl) |
| G2 | (structure: cyclohexyl-HN-imidazopyrazine with 3,4-dihydroxyphenyl) |
| H1 | (structure: cyclohexyl-HN-imidazopyrazine with 4,6-dichloropyrimidin-5-yl) |
| H2 | (structure: cyclohexyl-HN-imidazopyrazine with 5-fluoro-2-hydroxyphenyl) |

TABLE 3-continued

Compounds of Library 3

| Compound | |
|---|---|
| A3 | C4 |
| A4 | D3 |
| B3 | D4 |
| B4 | E3 |
| C3 | E4 |

TABLE 3-continued
Compounds of Library 3
| Compound | |
|---|---|
| 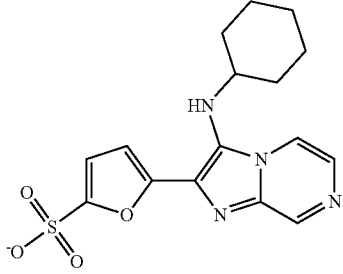 | F3 |
| 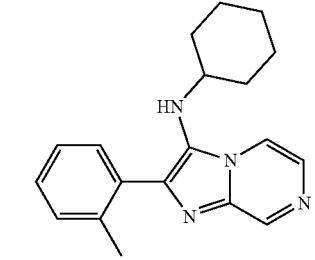 [SMILES: Cc1ccccc1-c1nc2cnccn2c1NC1CCCCC1] | F4 |
| 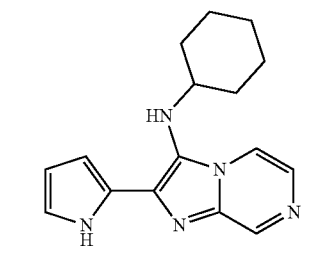 [SMILES: c1c[nH]c(-c2nc3cnccn3c2NC2CCCCC2)c1] | G3 |
| 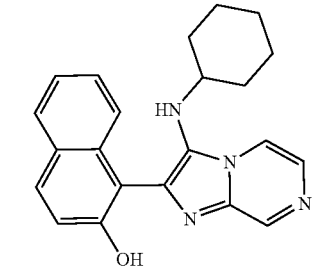 [SMILES: Oc1ccc2ccccc2c1-c1nc2cnccn2c1NC1CCCCC1] | G4 |
| 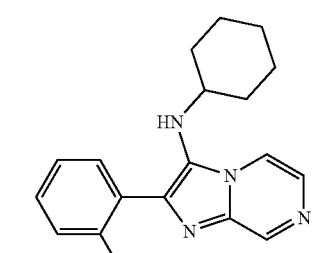 | H3 |
|  | H4 |
|  | A5 |
|  | A6 |
| 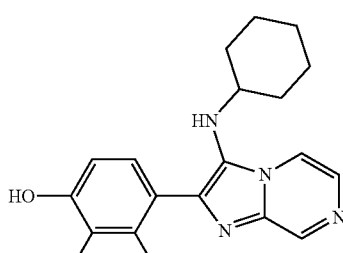 | B5 |
| 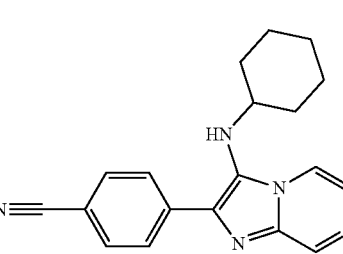 | B6 |
| DMSO | C5 |

TABLE 3-continued

Compounds of Library 3

| Compound | |
|---|---|
| C6 | F6 |
| D5 | G5 |
| D6 | G6 |
| E5 | H5 |
| E6 | H6 |
| F5 | A7 |

TABLE 3-continued
Compounds of Library 3
| Compound | |
|---|---|
| 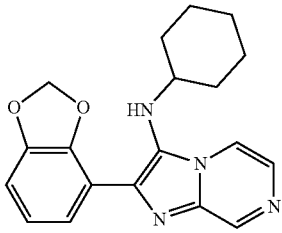 [SMILES: c1cc2c(c(-c3nc4cnccn4c3NC3CCCCC3)c1)OCO2] | A8 |
| 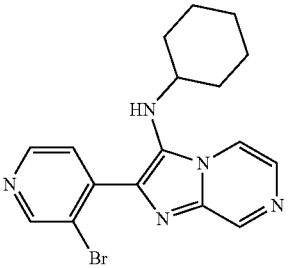 [SMILES: Brc1cnccc1-c1nc2cnccn2c1NC1CCCCC1] | B7 |
| 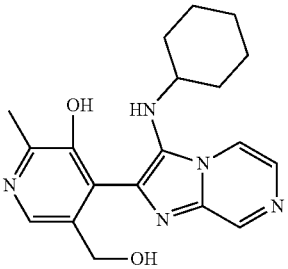 [SMILES: Cc1ncc(CO)c(-c2nc3cnccn3c2NC2CCCCC2)c1O] | B8 |
| 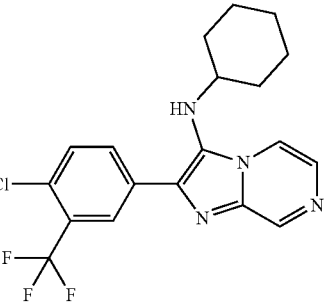 | C7 |
| 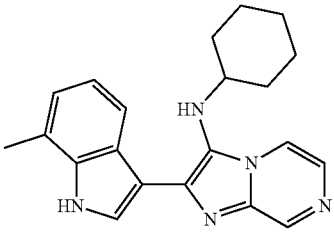 [SMILES: Cc1cccc2c(-c3nc4cnccn4c3NC3CCCCC3)c[nH]c12] | C8 |
TABLE 3-continued
Compounds of Library 3
| Compound | |
|---|---|
| 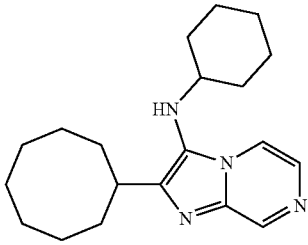 [SMILES: c1cn2c(NC3CCCCC3)c(C3CCCCCCC3)nc2cn1] | D7 |
| 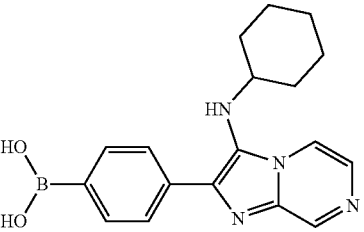 [SMILES: OB(O)c1ccc(-c2nc3cnccn3c2NC2CCCCC2)cc1] | D8 |
| 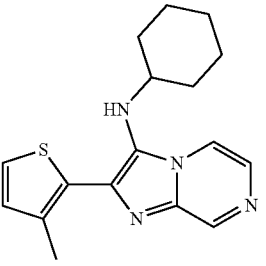 [SMILES: Cc1ccsc1-c1nc2cnccn2c1NC1CCCCC1] | E7 |
| 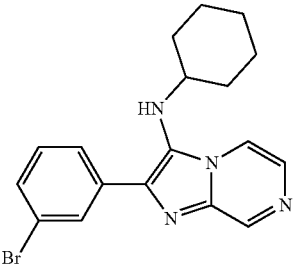 [SMILES: Brc1cccc(-c2nc3cnccn3c2NC2CCCCC2)c1] | E8 |
| 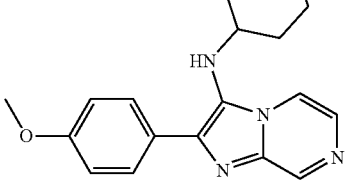 | F7 |
| 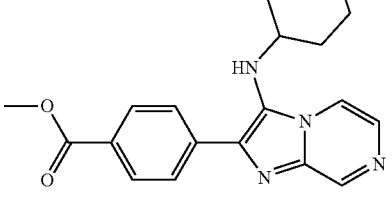 | F8 |
| DMSO | G7 |

TABLE 3-continued
Compounds of Library 3
| Compound | |
|---|---|
| 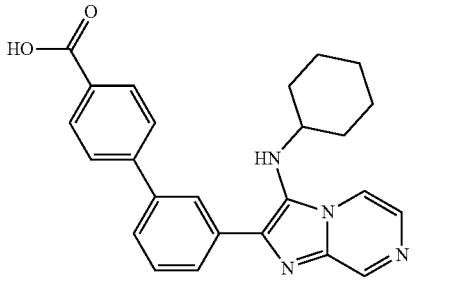 [SMILES: O=C(O)c1ccc(-c2cccc(-c3nc4cnccn4c3NC3CCCCC3)c2)cc1] | G8 |
| 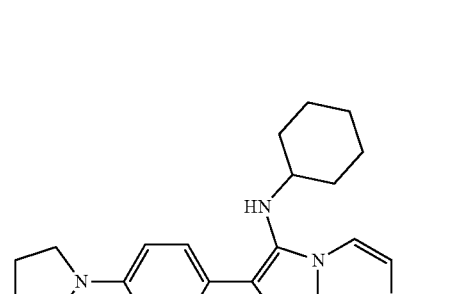 | H7 |
| 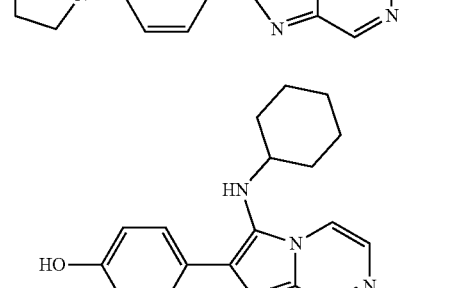 | H8 |
| 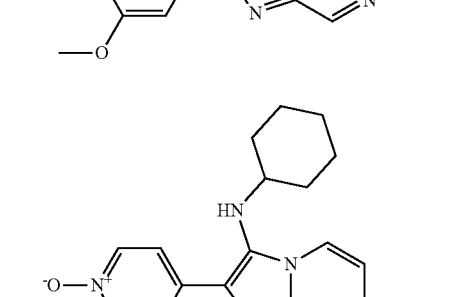 | A9 |
| 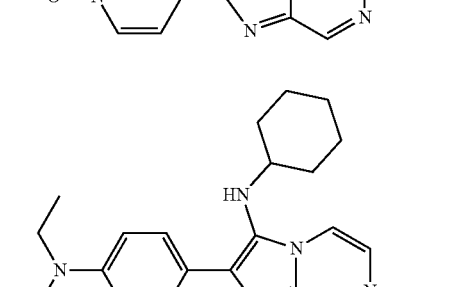 | A10 |
| 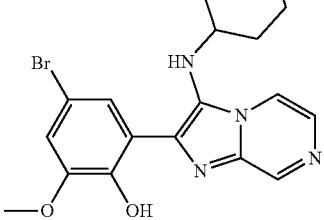 | B9 |
| 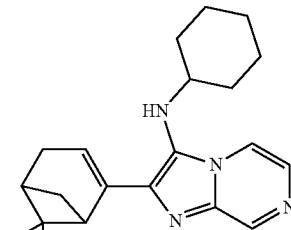 | B10 |
| 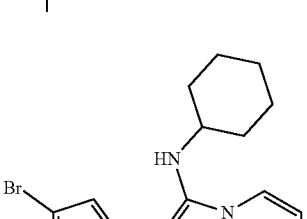 | C9 |
| 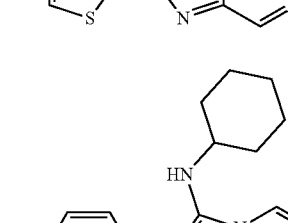 | C10 |
| Blank | D9 |
| 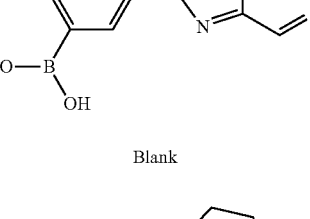 | D10 |

TABLE 3-continued

Compounds of Library 3

| Compound | |
|---|---|
| E9 | G10 |
| E10 | H9 |
| F9 | H10 |
| F10 | A11 |
| G9 | A12 |

TABLE 3-continued

Compounds of Library 3

| Compound | |
|---|---|
| (structure) | B11 |
| (structure) | B12 |
| (structure) | C11 |
| (structure) | C12 |
| (structure) | D11 |
| (structure) | D12 |
| (structure) | E11 |
| (structure) | E12 |
| DMSO | F11 |
| (structure) | F12 |
| (structure) | G11 |

TABLE 3-continued
Compounds of Library 3
Compound
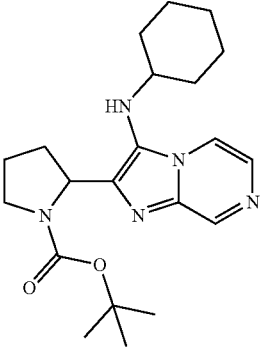 [SMILES: CC(C)(C)OC(=O)N1CCCC1c1nc2cnccn2c1NC1CCCCC1] G12
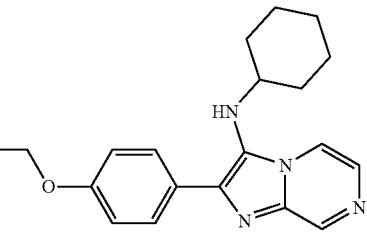 H11
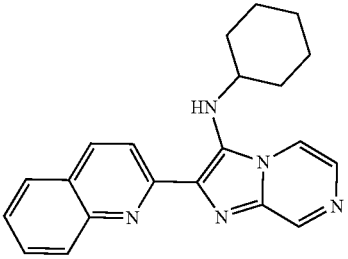 [SMILES: c1ccc2nc(-c3nc4cnccn4c3NC3CCCCC3)ccc2c1] H12
TABLE 4
Compounds of Library 4
Compound
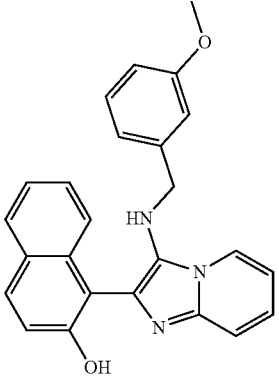 [SMILES: COc1cccc(CNc2c(-c3c(O)ccc4ccccc34)nc3ccccn23)c1] A1
TABLE 4-continued
Compounds of Library 4
Compound
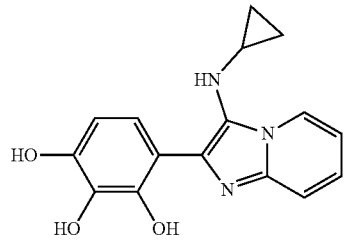 [SMILES: Oc1ccc(-c2nc3ccccn3c2NC2CC2)c(O)c1O] A2
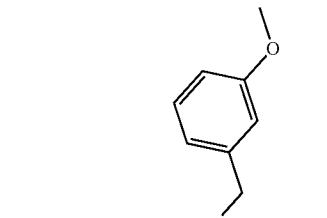 B1
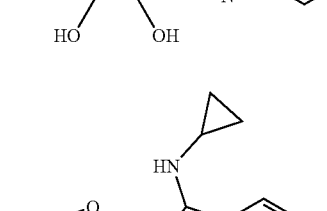 B2
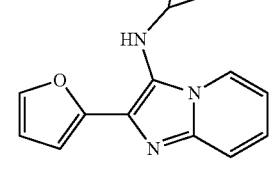 C1

TABLE 4-continued
Compounds of Library 4
| Compound | |
|---|---|
| C2 | 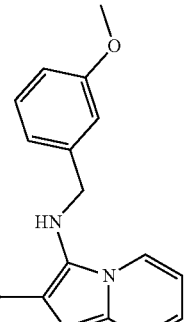 |
| D1 | 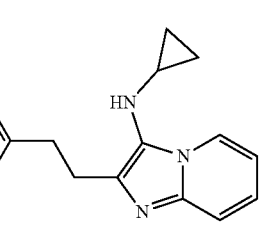 |
| D2 | 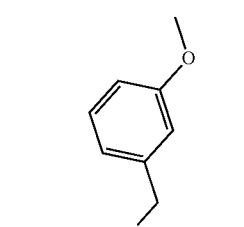 |
| E1 | 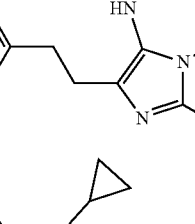 |
| E2 | 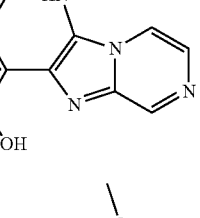 |
TABLE 4-continued
Compounds of Library 4
| Compound | |
|---|---|
| F1 | 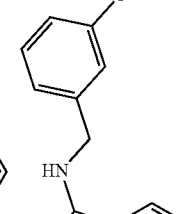 |
| F2 | 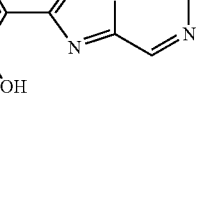 |
| G1 |  |
| G2 | 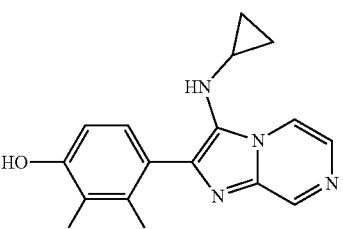 |
| H1 | 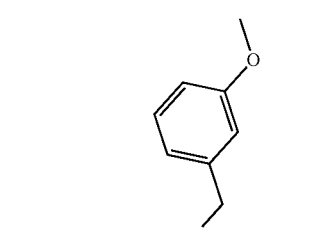 |

TABLE 4-continued

Compounds of Library 4

| Compound | |
|---|---|
| (structure) | H2 |
| (structure) | A3 |
| (structure) | A4 |
| (structure) | B3 |
| (structure) | B4 |
| (structure) | C3 |
| (structure) | C4 |
| (structure) | D3 |
| (structure) | D4 |

TABLE 4-continued

Compounds of Library 4

| Compound | |
|---|---|
| (structure: 3-chlorobenzyl-NH imidazopyrazine with 2-hydroxynaphthyl) | E3 |
| (structure: morpholinoethyl-NH imidazopyrazine with 2-hydroxynaphthyl) | E4 |
| (structure: 3-chlorobenzyl-NH imidazopyrazine with 2,3,4-trihydroxyphenyl) | F3 |
| (structure: morpholinoethyl-NH imidazopyrazine with 2,3,4-trihydroxyphenyl) | F4 |
| (structure: 3-chlorobenzyl-NH imidazopyrazine with 2-furyl) | G3 |
| (structure: morpholinoethyl-NH imidazopyrazine with 2-furyl) | G4 |
| (structure: 3-chlorobenzyl-NH imidazopyrazine with 4-tert-butylphenethyl) | H3 |
| (structure: morpholinoethyl-NH imidazopyrazine with 4-tert-butylphenethyl) | H4 |
| (structure: 4-methoxyphenyl-NH imidazopyridine with 2-hydroxynaphthyl) | A5 |

TABLE 4-continued
Compounds of Library 4
| Compound | |
|---|---|
| 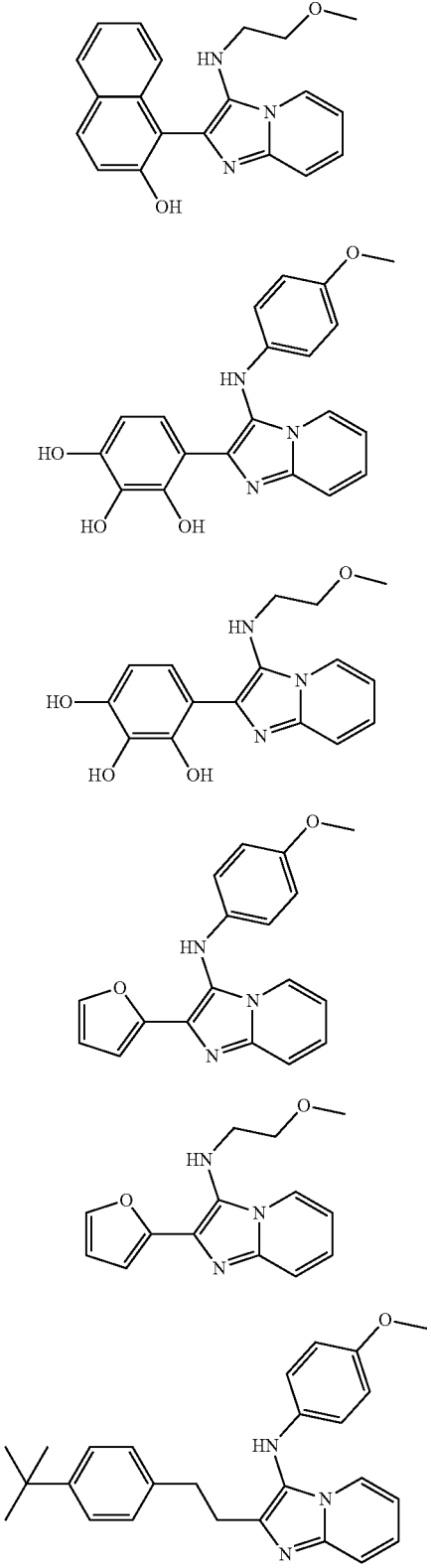 | A6 |
| | B5 |
| | B6 |
| | C5 |
| | C6 |
| | D5 |
TABLE 4-continued
Compounds of Library 4
| Compound | |
|---|---|
| 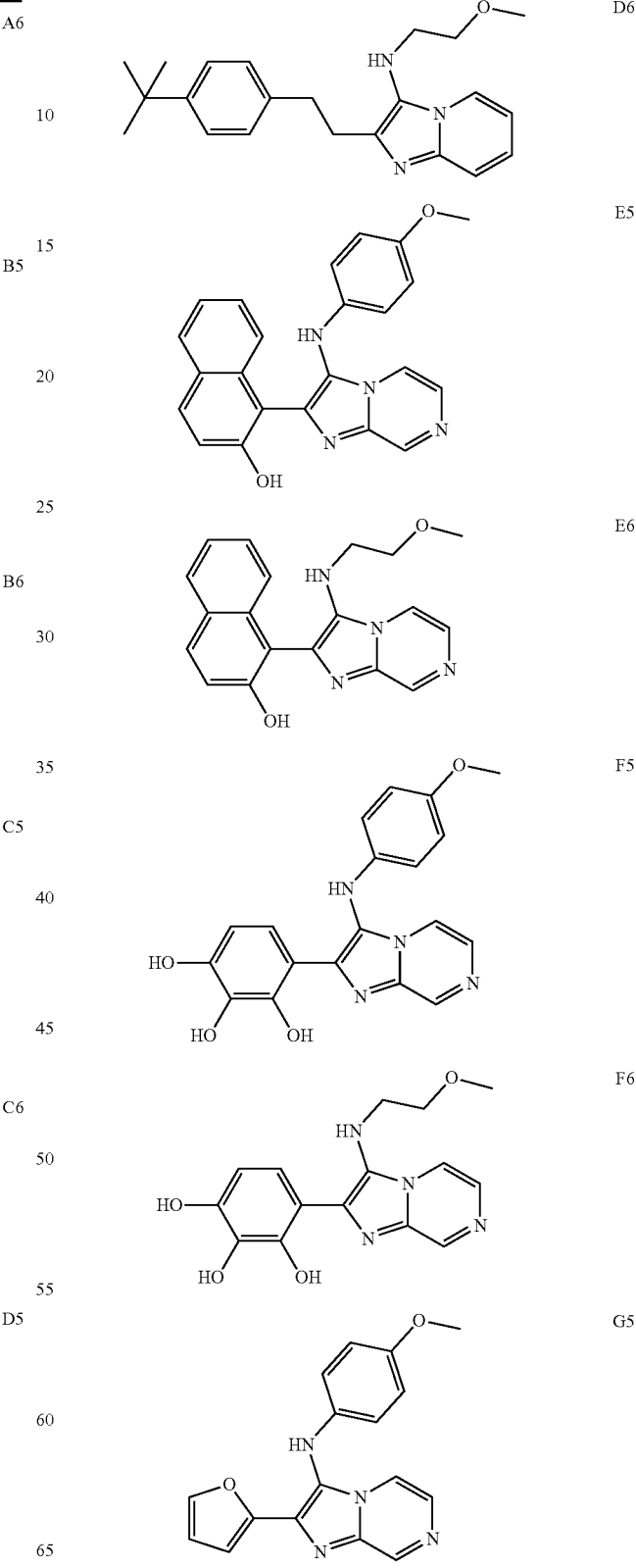 | D6 |
| | E5 |
| | E6 |
| | F5 |
| | F6 |
| | G5 |

TABLE 4-continued

Compounds of Library 4

| Compound |
| --- |
| G6 |
| H5 |
| H6 |
| A7 |
| A8 |

TABLE 4-continued

Compounds of Library 4

| Compound |
| --- |
| B7 |
| B8 |
| C7 |
| C8 |
| D7 |

TABLE 4-continued

Compounds of Library 4

| Compound | |
|---|---|
| (structure) | D8 |
| (structure) | E7 |
| (structure) | E8 |
| (structure) | F7 |
| (structure) | F8 |
| (structure) | G7 |
| (structure) | G8 |
| (structure) | H7 |
| (structure) | H8 |
| (structure) | A9 |

TABLE 4-continued

Compounds of Library 4

| Compound | |
|---|---|
| (structure) | A10 |
| (structure) | B9 |
| (structure) | B10 |
| (structure) | C9 |
| (structure) | C10 |
| (structure) | D9 |
| (structure) | D10 |
| (structure) | E9 |
| (structure) | E10 |
| (structure) | F9 |

TABLE 4-continued
Compounds of Library 4
Compound
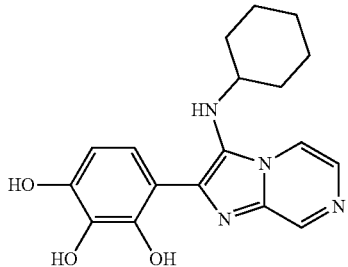 [SMILES: Oc1ccc(-c2nc3cnccn3c2NC2CCCCC2)c(O)c1O] F10
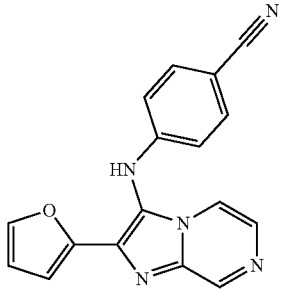 [SMILES: N#Cc1ccc(Nc2c(-c3ccco3)nc3cnccn23)cc1] G9
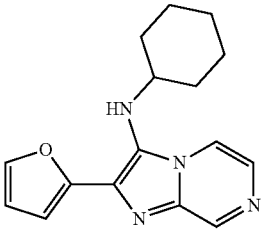 [SMILES: c1coc(-c2nc3cnccn3c2NC2CCCCC2)c1] G10
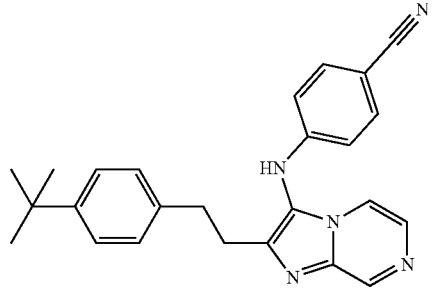 [SMILES: CC(C)(C)c1ccc(CCc2nc3cnccn3c2Nc2ccc(C#N)cc2)cc1] H9
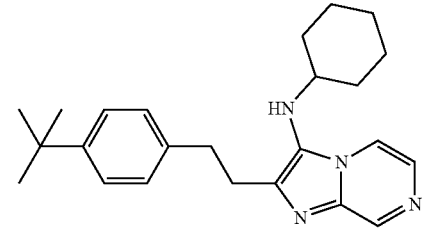 [SMILES: CC(C)(C)c1ccc(CCc2nc3cnccn3c2NC2CCCCC2)cc1] H10
TABLE 4-continued
Compounds of Library 4
Compound
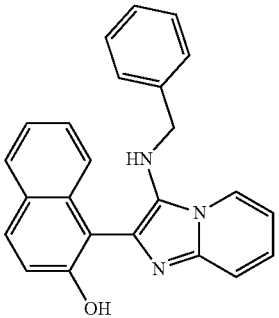 [SMILES: Oc1ccc2ccccc2c1-c1nc2ccccn2c1NCc1ccccc1] A11
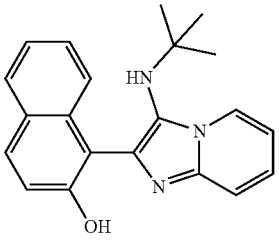 [SMILES: CC(C)(C)Nc1c(-c2c(O)ccc3ccccc23)nc2ccccn12] A12
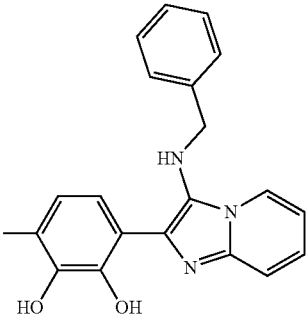 B11
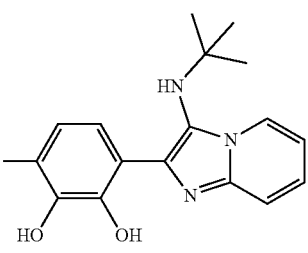 B12
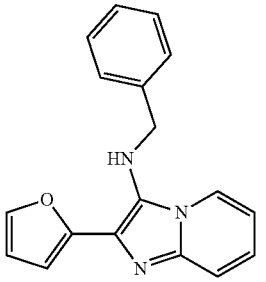 [SMILES: c1ccc(CNc2c(-c3ccco3)nc3ccccn23)cc1] C11

TABLE 4-continued

Compounds of Library 4

Compound

C12, D11, D12, E11, E12, F11, F12, G11, G12, H11

TABLE 4-continued

Compounds of Library 4

Compound

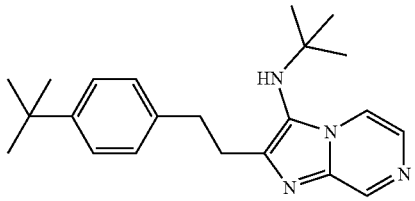 [SMILES: CC(C)(C)Nc1c(CCc2ccc(C(C)(C)C)cc2)nc2cnccn12]

H12

II. Pharmaceutical Compositions

In certain embodiments, the present invention provides pharmaceutical compositions comprising a compound of Formula I and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I or Formula II. As another example, the salt may comprise less than one inorganic or organic acid molecule per molecule of base, such as two molecules of compound of Formula I or Formula II per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

III. Uses of Compounds and Compositions

In certain aspects, the invention provides methods of treating or preventing a disease or condition, comprising administering to a subject a compound of one of Formula I, e.g., in a therapeutically effective amount or a composition comprising a compound of Formula I.

In some embodiments, the disease is cancer. In some embodiments, the cancer is selected from acute myeloid leukemia, liver cancer, lung cancer, and myelodysplastic syndromes (MDS).

In certain embodiments, the cancer is a solid tumor. For example, the subject is generally one who has been diagnosed as having a cancerous tumor or one who has been previously treated for a cancerous tumor (e.g., where the tumor has been previously removed by surgery). The cancerous tumor may be a primary tumor and/or a secondary (e.g., metastatic) tumor.

In certain embodiments, the subject is a mammal, e.g., a human.

In certain embodiments, the invention provides methods of inhibiting proliferation of a cancerous cell comprising contacting a cancerous cell with an effective amount of a compound of one of Formula I or a composition comprising a compound of one of Formula I.

IV. Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —OCF$_3$, ethoxy, propoxy, tert-butoxy and the like.

The term "cycloalkyloxy" refers to a cycloakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "$C_{x\text{-}y}$" when used in conjunction with a chemical moiety, such as acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

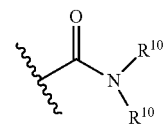

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

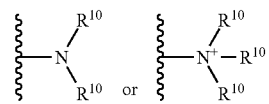

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

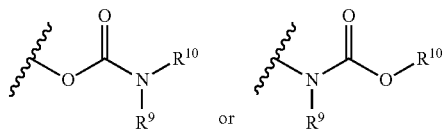

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteralkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, benzimidazole, quinoline, isoquinoline, quinoxaline, quinazoline, indole, isoindole, indazole, benzoxazole, pyrazine, pyridazine, purine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

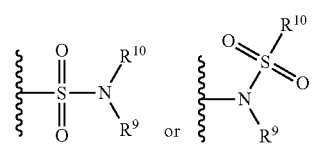

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

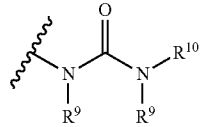

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of Formula I in a formulation represented above can be replaced with the corresponding suitable prodrug, e.g., wherein a hydroxyl in the parent compound is presented as an ester or a carbonate or carboxylic acid present in the parent compound is presented as an ester.

EXAMPLES

Example 1: Chemical Syntheses

The compounds disclosed herein were prepared via a Groebke-Blackburn-Bienayme Multicomponent Reaction as highlighted in Scheme 1.

Scheme 1

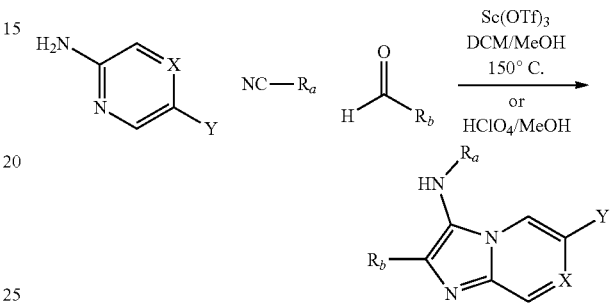

Library 1 Synthesis

Each amine (A1-A3), isocyanide (B1 and B2) and aldehyde (C1-C10) was prepared as 400 mM DMSO solution. (See Table 5). Sc(OTf)$_3$ was prepared as a 20 mM DMSO solution. In each well on a 96 well plate, a different combination of 20 uL of the 400 mM solutions of an amine, isocyanide, aldehyde (1.0 equivalents each), as detailed by the plate map, and Sc(OTf)$_3$ (0.05 equivalents) was combined to give final concentrations of 100 mM product. To the outer wells of the plate were added 100 uL of DMSO. Once all components were added to a plate, the plate was sealed and centrifuged at 1000×g for 30 s. The plate was then placed in an oven at 110° C. overnight (15 h). Reactions were spot checked for product conversion by LCMS. Plate was submitted for assay testing.

TABLE 5

Reaction components for Library 1

Amines: A1, A2, A3

Isocyanides: B1, B2

Aldehyde: C1, C2, C3

TABLE 5-continued

Reaction components for Library 1

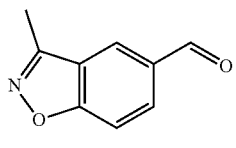
C4

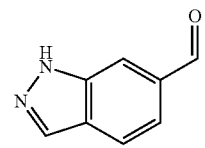
C5

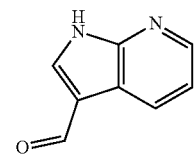
C6

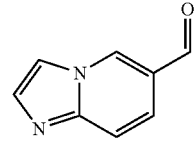
C7

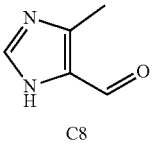
C8

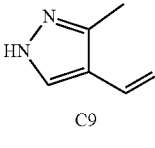
C9

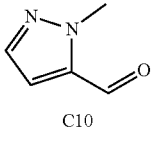
C10

Library 2 Synthesis

Each amine (A1-A3), isocyanide (B1 and B2) and aldehyde (C1-C10) was prepared as 400 mM DMSO solution. Sc(OTf)$_3$ was prepared as a 20 mM DMSO solution. (See Table 6). In each well on a 96 well plate, a different combination of 20 uL of the 400 mM solutions of an amine, isocyanide, aldehyde (1.0 equivalents each), as detailed by the plate map, and Sc(OTf)$_3$ (0.05 equivalents) was combined to give final concentrations of 100 mM product. To the outer wells of the plate were added 100 uL of DMSO. Once all components were added to a plate, the plate was sealed and centrifuged at 1000×g for 30 s. The plate was then placed in an oven at 110° C. overnight (15 h). Reactions were spot checked for product conversion by LCMS. Plate was submitted for assay testing.

TABLE 6

Reaction components for Library 2

Amines

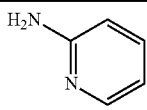
A1

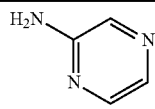
A2

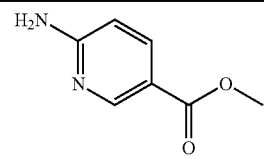
A3

Isocyanides

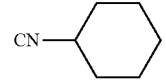
B1

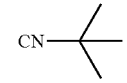
B2

Aldehyde

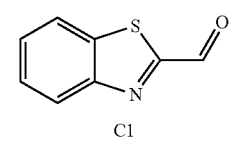
C1

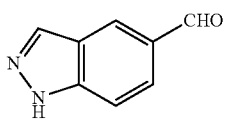
C2

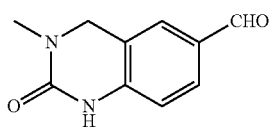
C3

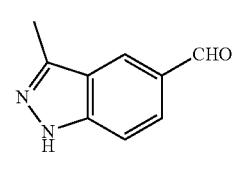
C4

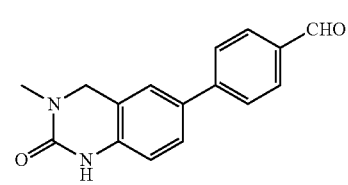
C5

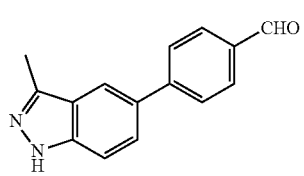
C6

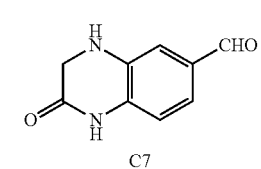
C7

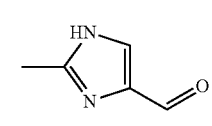
C8

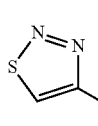
C9

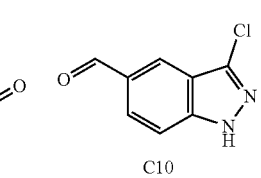
C10

Library 3 Synthesis 2-aminopyrazine (23.8 mg, 0.25 mmol) and Sc(OTf)3 (6.2 mg, 0.013 mmol) were combined and suspended in DMSO (2.5 mL). To the reaction was then added cyclohexylisocyanide (31.1 uL, 0.25 mmol). The mixture was then added to a 96 well plate, adding 25 uL/well. To each well containing the reaction mixture, 25 uL of a 100 mM solution of an aldehyde was added. The plate was then sealed, centrifuged at 1000×g for 30 s and placed in an oven at 100° C. overnight (17 h). Reactions were spot checked for product conversion by LCMS. Plate was submitted for assay testing.

Library 4 Synthesis

Each amine (A1 and A2), isocyanide (I1-I12) and aldehyde (B1-B4) was prepared as 400 mM DMSO solution. (See Table 7). Sc(OTf)$_3$ was prepared as a 20 mM DMSO solution. In each well on a 96 well plate, a different combination of 10 uL of the 400 mM solutions of an amine, isocyanide, aldehyde (1.0 equivalents each), as detailed by the plate map, and Sc(OTf)$_3$ (0.05 equivalents) was combined to give final concentrations of 100 mM product. Once all components were added to a plate, the plate was sealed and centrifuged at 1000×g for 30 s. The plate was then placed in an oven at 100° C. overnight. Reactions were spot checked for product conversion by LCMS. Plate was submitted for assay testing.

TABLE 7

Reaction components for Library 4

Amines

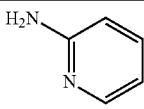

A1

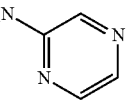

A2

Isocyanides

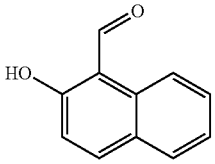

B1

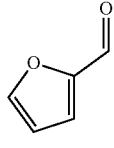

B2

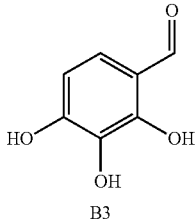

B3

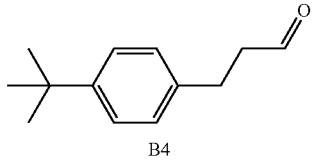

B4

Aldehyde

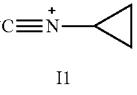

I1

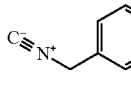

I2

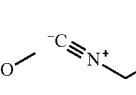

I3

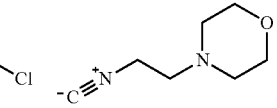

I4

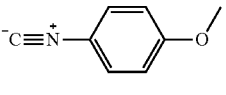

I5

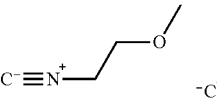

I6

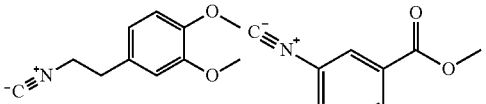

I7

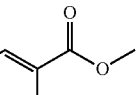

I8

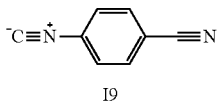

I9

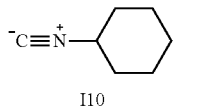

I10

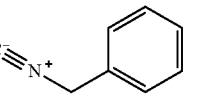

I11

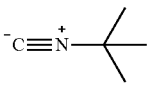

I12

87
Library 1, Compound C10

Scheme 2

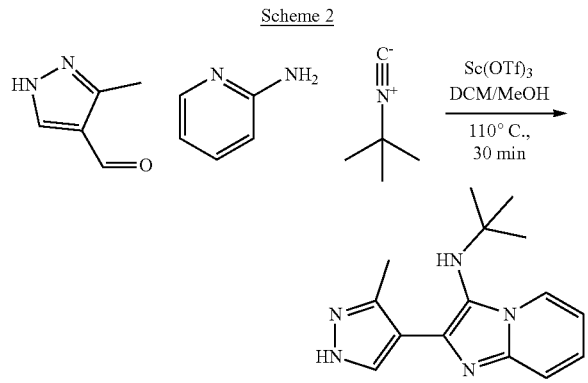

3-methyl-1H-pyrazole-4-carbaldehyde (44.2 mg, 0.40 mmol) and 2-aminopyridine (48.7 mg, 0.52 mmol) were combined and suspended in 3:1 DCM/MeOH (2 mL). To the reaction was then added tert-butyl isocyanide (58.8 uL, 0.52 mmol) followed by Sc(OTf)$_3$ (10.0 mg, 0.02 mmol). The reaction was heated via microwave to 110° C. for 30 minutes. Reaction was filtered, washed with EtOAc and concentrated to dryness on the rotovap. Crude compound was purified via ISCO chromatography (0-10% MeOH:DCM). Product yield: 16.8 mg, 15.6%
Library 1, Compound E10

Scheme 3

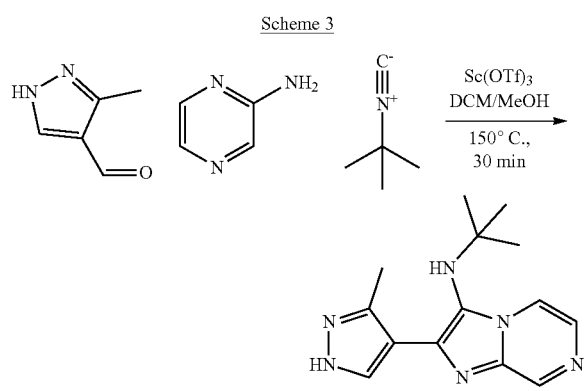

3-methyl-1H-pyrazole-4-carbaldehyde (44.1 mg, 0.40 mmol) and 2-aminopyrazine (49.6 mg, 0.52 mmol) were combined and suspended in 3:1 DCM/MeOH (2 mL). To the reaction was then added tert-butyl isocyanide (58.8 uL, 0.52 mmol) followed by Sc(OTf)$_3$ (10.2 mg, 0.02 mmol). The reaction was heated via microwave to 110° C. for 30 minutes. Reaction was filtered, washed with EtOAc and concentrated to dryness on the rotovap. Crude compound was purified via ISCO chromatography (0-10% MeOH:DCM). Product yield: 26.7 mg, 24.7%
Library 1, Compound D6

Scheme 4

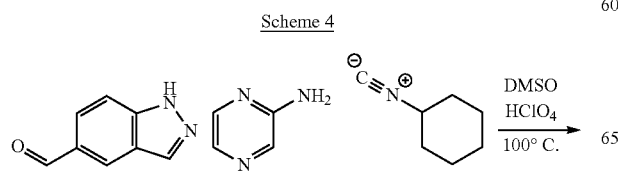

88

-continued

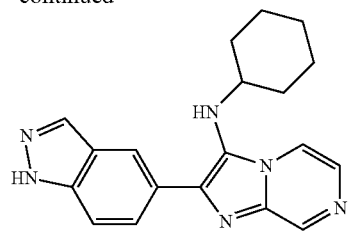

1H-indazole-5-carbaldehyde (58.7 mg, 0.40 mmol) and pyrazin-2-amine (38.2 mg, 0.40 mmol) were combined and suspended in DMSO (2 mL). To the reaction was then added isocyanocyclohexane (49.9 uL, 0.40 mmol) followed by HClO$_4$ (1.2 uL, 0.02 mmol). The reaction was heated to 100° C. for 2 hours. Reaction was quenched with H2O and desired product precipitated out. Reaction was filtered and the crude precipitate was purified via ISCO chromatography (0-100% EtOAc:Hexanes). Product yield: 18.8 mg, 14.1%
Library 4, Compound A1

Scheme 5

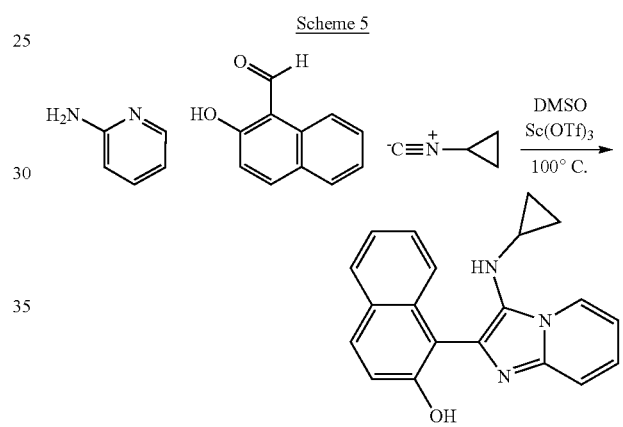

Pyridin-2-amine (0.40 mmol), 2-hydroxy-1-naphthaldehyde (0.80 mmol) and isocyanocyclopropane (0.15 mmol) were prepared as 400 mM solutions in DMSO and combined. Sc(OTf)$_3$ (0.003 mmol) was added as a 20 mM DMSO solution to the reaction. Reaction was heated to 100° C. overnight. Reaction was purified via HPLC.
Library 4, Compound A12

Scheme 6

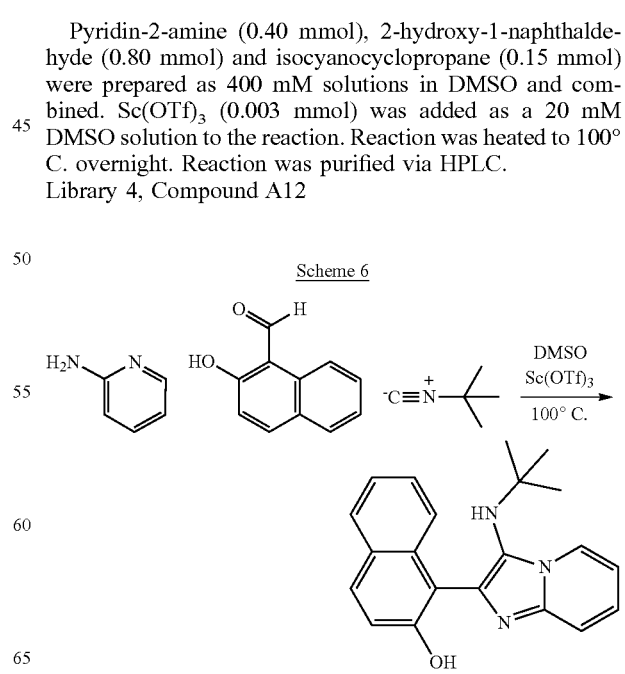

Pyridin-2-amine (0.40 mmol), 2-hydroxy-1-naphthaldehyde (0.80 mmol) and 2-isocyano-2-methylpropane (0.40 mmol) were prepared as 400 mM solutions in DMSO and combined. Sc(OTf)$_3$ (0.003 mmol) was added as a 20 mM DMSO solution to the reaction. Reaction was heated to 100° C. overnight. Reaction was purified via HPLC.
Library 4, Compound E1

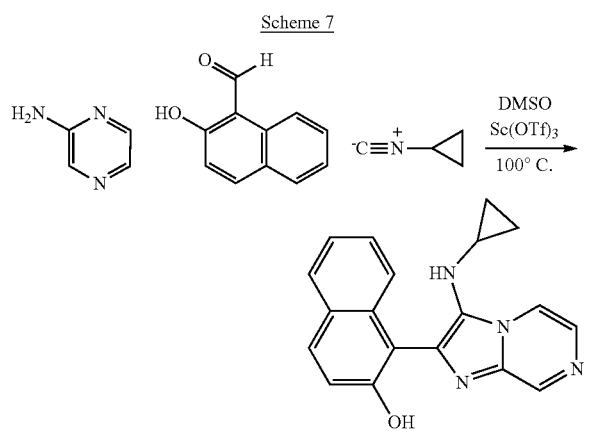

Scheme 7

Pyrazin-2-amine (0.40 mmol), 2-hydroxy-1-naphthaldehyde (0.80 mmol) and isocyanocyclopropane (0.15 mmol) were prepared as 400 mM solutions in DMSO and combined. Sc(OTf)$_3$ (0.003 mmol) was added as a 20 mM DMSO solution to the reaction. Reaction was heated to 100° C. overnight. Reaction was purified via HPLC.
Library 4, Compound E2

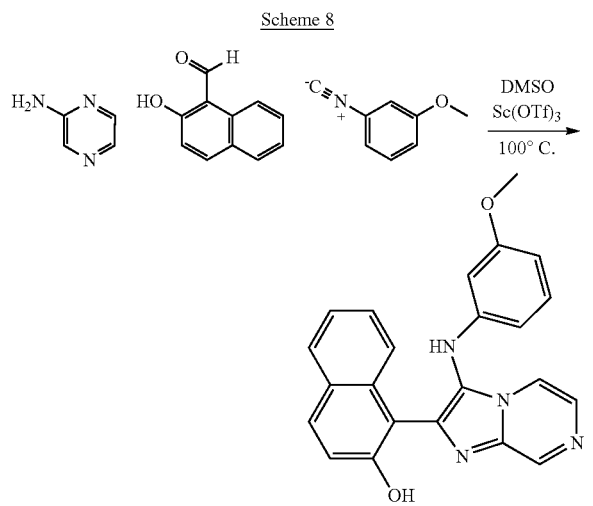

Scheme 8

Pyrazin-2-amine (0.40 mmol), 2-hydroxy-1-naphthaldehyde (0.80 mmol) and 2-isocyano-3-methoxybenzene (0.44 mmol) were prepared as 400 mM solutions in DMSO and combined. Sc(OTf)$_3$ (0.003 mmol) was added as a 20 mM DMSO solution to the reaction. Reaction was heated to 100° C. overnight. Reaction was purified via HPLC.

Example 2

A biochemical assay was developed based on the AlphaScreen assay to monitor the inhibition of SALL4.

Table 8 highlights exemplary data from the AlphaScreen assay for compounds of Formula I. SRI 311 is a control compound.

TABLE 8

Assay Data from compounds of Library 4

| Compound | IC50 µM |
|---|---|
| A1 | 0.1093 |
| A4 | 2.231 |
| A10 | 2.77 |
| A11 | 1.506 |
| A12 | 0.1616 |
| E1 | 0.3347 |
| E2 | 0.2876 |
| E4 | 1.357 |
| E5 | 0.6193 |
| E6 | 0.4339 |
| E7 | 2.489 |
| E8 | 0.6226 |
| E9 | 0.4976 |
| E10 | 0.6157 |
| E11 | 0.5938 |
| E12 | 0.7834 |
| SRI 311 | ~3.575 |

Example 3

The biological activity of lead compounds was assessed in a cellular assay. Table 9 highlights exemplary data from the WST8/Cell Titer Viability Assay for compounds of Formula I.

TABLE 9

Assay Data for compounds of Library 4

| Compound | WST8 H549 | WST8 H611 | Cell Titer H549 | Cell Titer H611 |
|---|---|---|---|---|
| A1 | 27.45 | 6.67 | 37.37 | 13.16 |
| A4 | 38.17 | 15.58 | ~36.75 | 14.01 |
| A10 | >100 | 25.8 | >100 | 27.39 |
| A11 | 23.78 | 8.292 | 40.92 | 11.14 |
| A12 | 26.6 | 10.12 | 22.47 | 7.808 |
| E1 | >100 | 15.22 | >100 | 19.4 |
| E2 | >100 | 17.82 | >100 | 19.56 |
| E4 | >100 | 23.53 | >100 | 24.41 |
| E5 | >100 | 26.97 | >100 | 41.43 |
| E6 | >100 | 43.54 | >100 | ~42.85 |
| E7 | 46.33 | 58.92 | >100 | ~40.18 |
| E8 | 34.93 | ~38.92 | >100 | ~41.47 |
| E9 | NA | NA | NA | NA |
| E10 | 18.66 | 20.95 | >100 | ~39.60 |
| E11 | 75.14 | 98.13 | >100 | ~43.93 |
| E12 | >100 | >100 | >100 | >100 |
| A9 | 9.095 | 10.28 | ~40.41 | 13.65 |
| SRI 311 | 3.203 | 3.448 | 29.26 | 8.444 |
| SRI 027 | 25.19 | 29.66 | 30.08 | 29.71 |
| Vandy001 | >100 | >100 | >100 | >100 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound having a structure of Formula I or a pharmaceutically acceptable salt thereof:

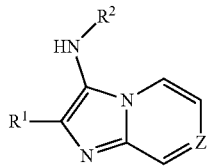

Formula I wherein

Z is N;

R¹ is optionally substituted C₅ or C₆-cycloalkyl, optionally substituted heterocyclyl, naphthalenyl substituted with one or more groups selected from hydroxyl and nitro,

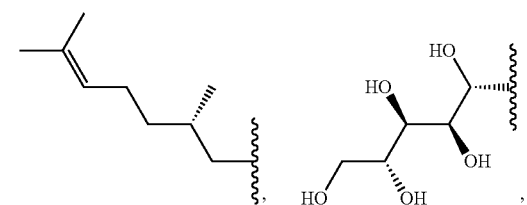

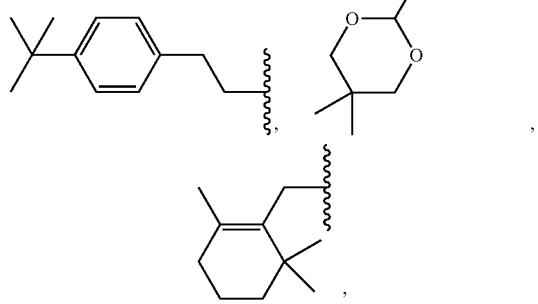

optionally substituted oxazolyl, optionally substituted benzoisoxazolyl, optionally substituted indazolyl, optionally substituted azaindolyl, optionally substituted benzothiazolyl, optionally substituted thiazolyl, or optionally substituted carbazolyl; and R² is optionally substituted alkyl, optionally substituted cycloalkyl, optionally substituted heterocyclyl, optionally substituted aryl, or optionally substituted heteroaryl.

2. The compound of claim 1, wherein R¹ is naphthalenyl substituted with one or more groups selected from hydroxyl and nitro.

3. The compound of claim 2, wherein R¹ is selected from

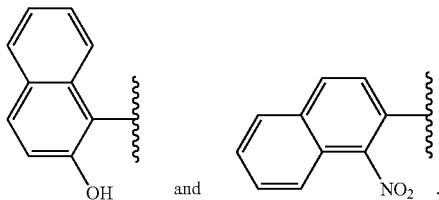

4. The compound of claim 1, wherein R¹ is selected from

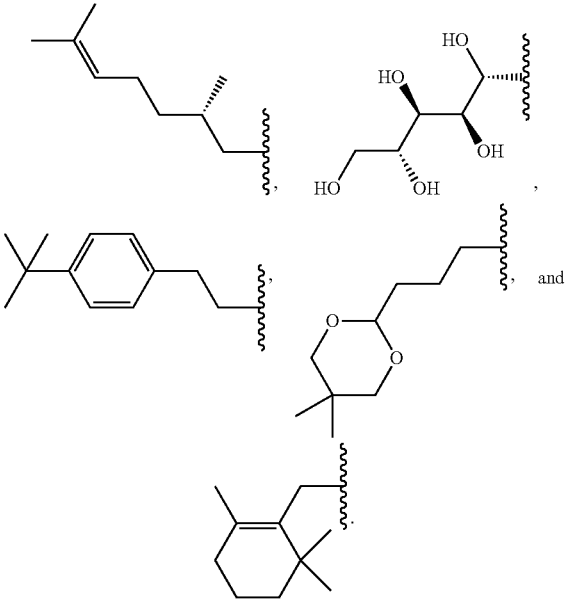

5. The compound of claim 1, wherein R¹ is optionally substituted C₅ or C₆-cycloalkyl or optionally substituted heterocyclyl.

6. The compound of claim 5, wherein R¹ is selected from

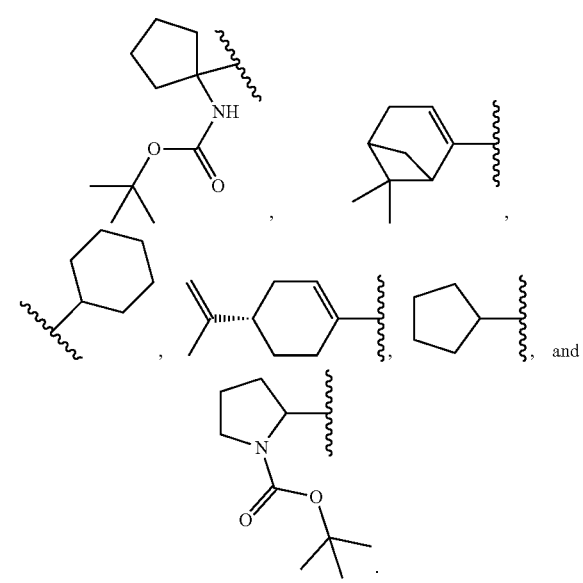

7. The compound of claim 1, wherein R¹ is optionally substituted oxazolyl, optionally substituted benzoisoxazolyl, optionally substituted indazolyl, optionally substituted azaindolyl, optionally substituted benzothiazolyl, optionally substituted thiazolyl, and optionally substituted carbazolyl.

8. The compound of claim 7, wherein R¹ is substituted with one or more groups selected from halo, oxy, nitro, sulfonate, and optionally substituted alkyl.

9. The compound of claim 8, wherein R¹ is selected from

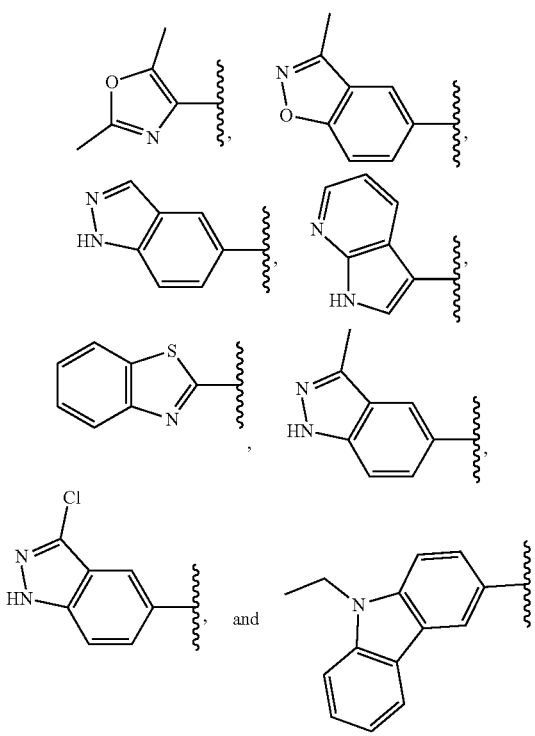

10. The compound of claim 1, wherein R² is optionally substituted alkyl, optionally substituted cycloalkyl, or optionally substituted aryl.

11. The compound of claim 10, wherein the alkyl is substituted with alkoxy, amino or optionally substituted aryl.

12. The compound of claim 10, wherein R² is selected from

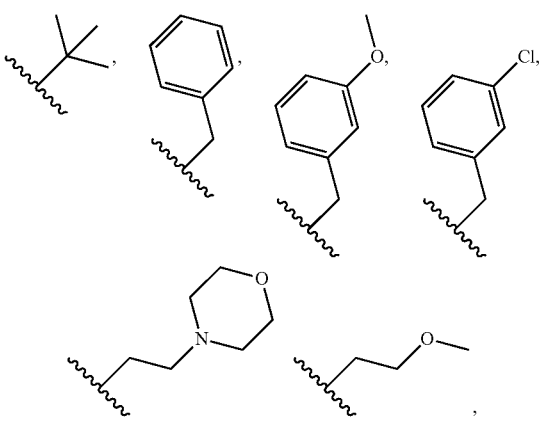

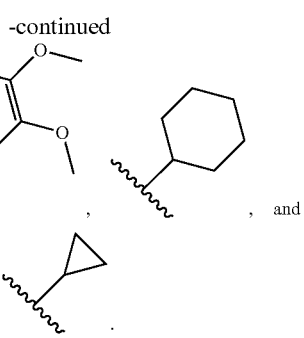

13. The compound of claim 10, wherein R² is optionally substituted phenyl.

14. The compound of claim 13, wherein the phenyl is substituted with one more groups selected from halo, hydroxyl, cyano, optionally substituted alkyl, optionally substituted alkoxy, carboxy, and ester.

15. The compound of claim 14, wherein R² is selected from

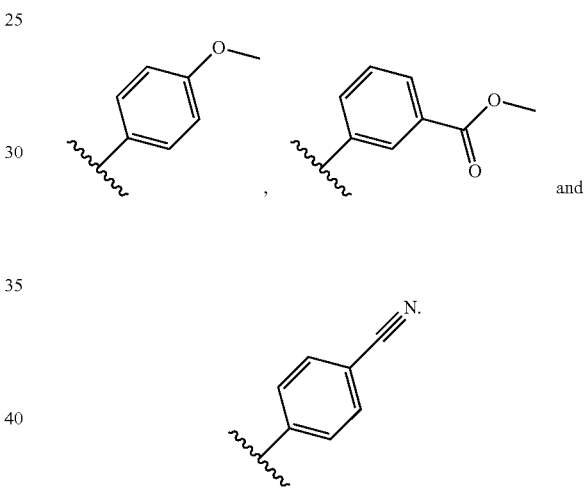

16. A pharmaceutical composition comprising the compound or pharmaceutically acceptable salt thereof of claim 1 and a pharmaceutically acceptable carrier.

17. A method of treating cancer, wherein the cancer is acute myeloid leukemia, liver cancer, lung cancer, or myelodysplastic syndromes (MDS) comprising administering to a subject the compound or pharmaceutically acceptable salt thereof of claim 1.

18. A compound which is

B1-Library 3

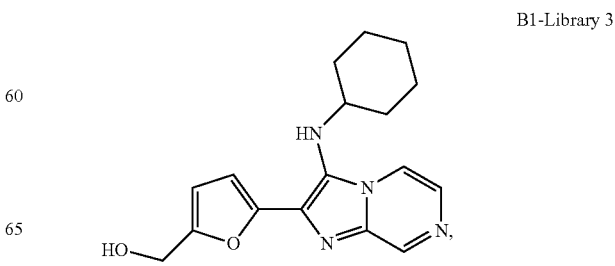

A2-Library 3
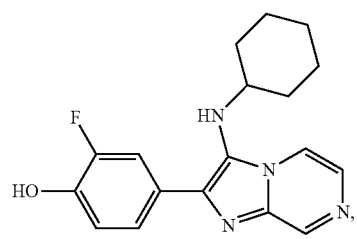
B2-Library 3
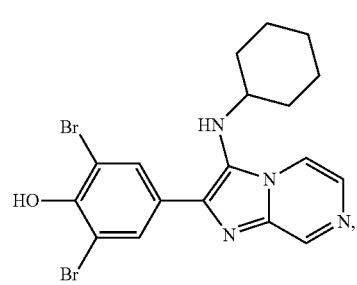
D1-Library 3
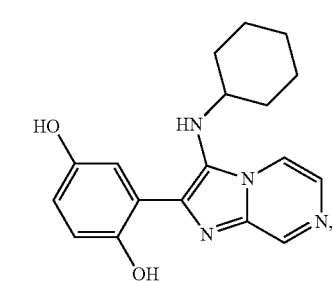
C2-Library 3
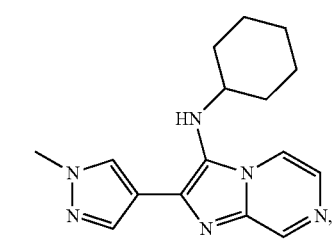
E1-Library 3
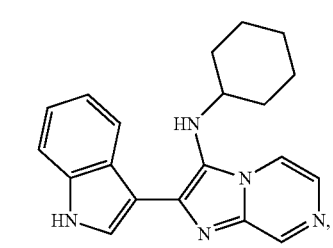
D2-Library 3
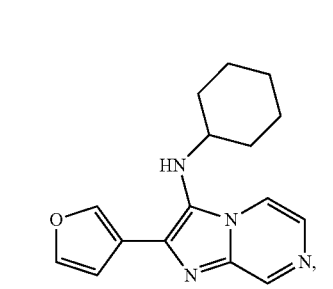
F1-Library 3
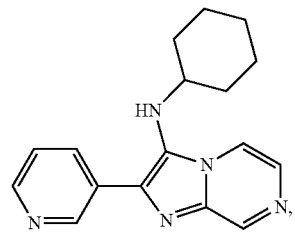
E2-Library 3
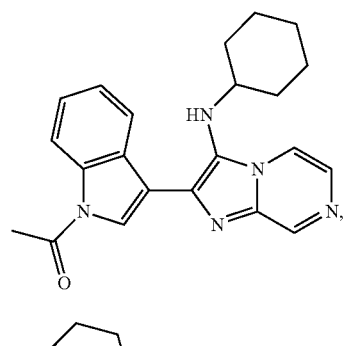
G1-Library 3
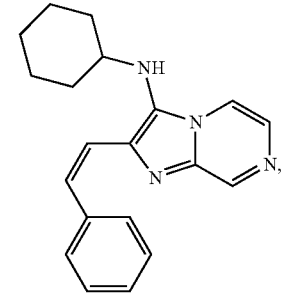
F2-Library 3
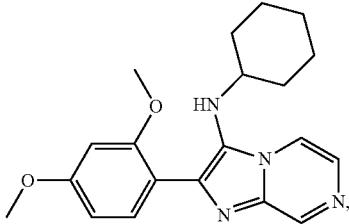
H1-Library 3
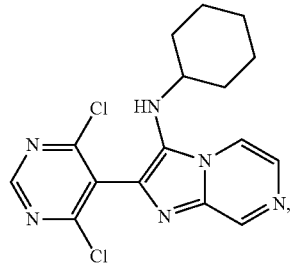
G2-Library 3
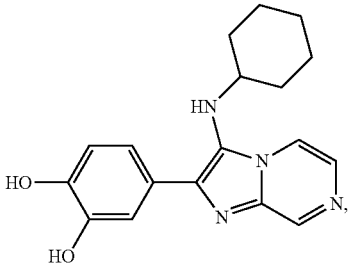

A3-Library 3
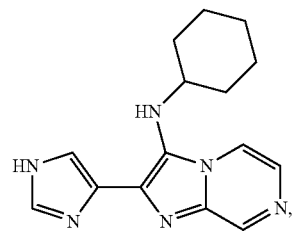
H2-Library 3
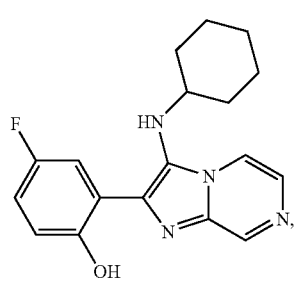
B3-Library 3
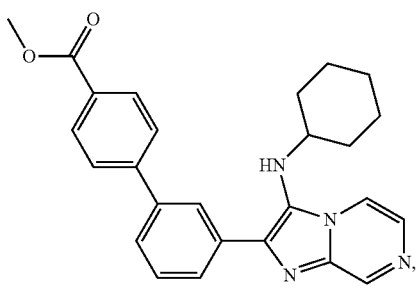
A4-Library 3
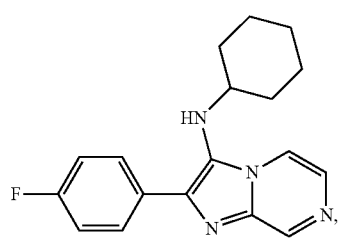
C3-Library 3
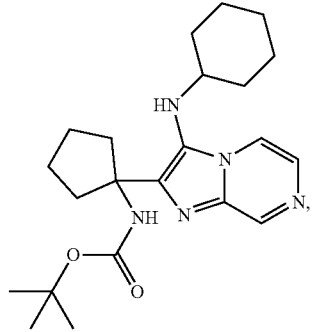
B4-Library 3
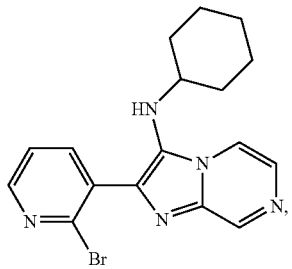
D3-Library 3
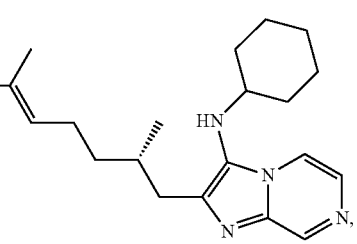
C4-Library 3
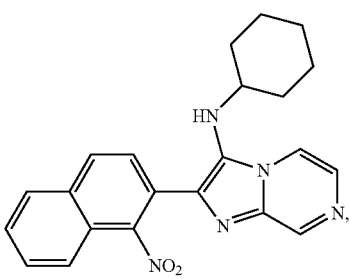
E3-Library 3
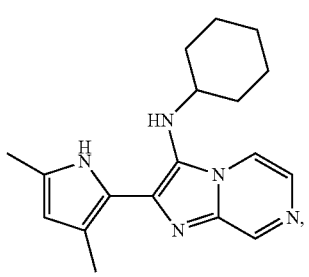
D4-Library 3
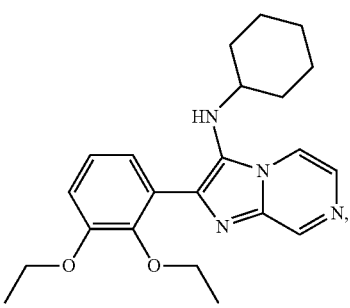

99
-continued
F3-Library 3
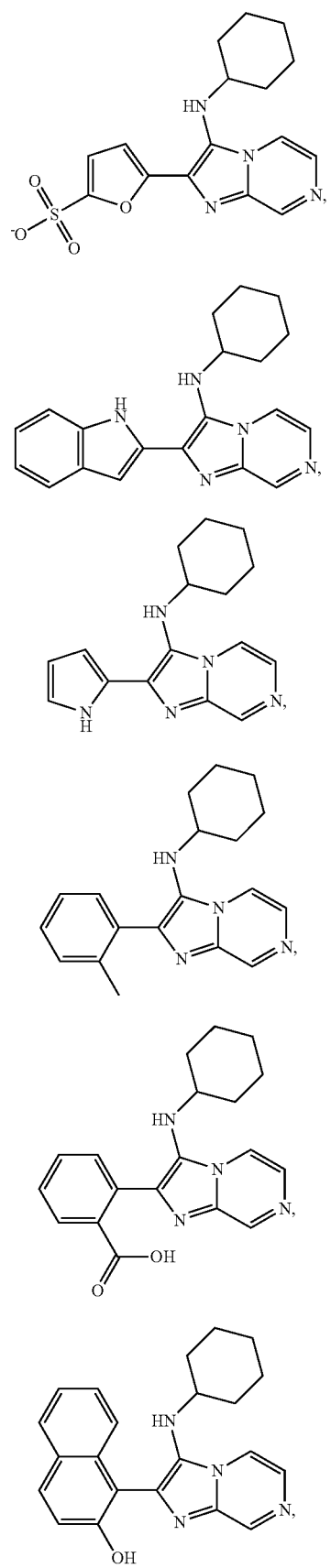
E4-Library 3
G3-Library 3
F4-Library 3
H3-Library 3
G4-Library 3
100
-continued
A5-Library 3
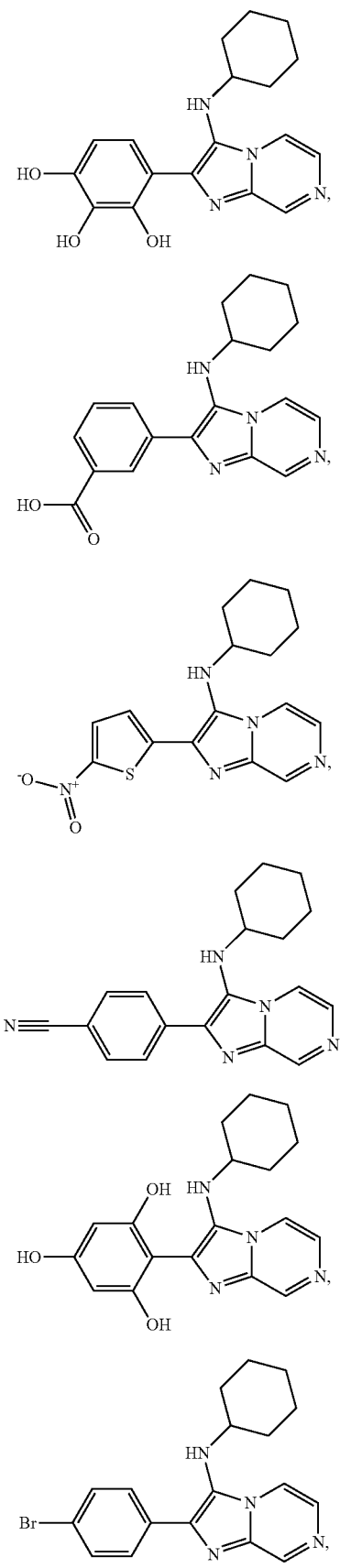
H4-Library 3
B5-Library 3
A6-Library 3
D5-Library 3
B6-Library 3

101
-continued
E5-Library 3
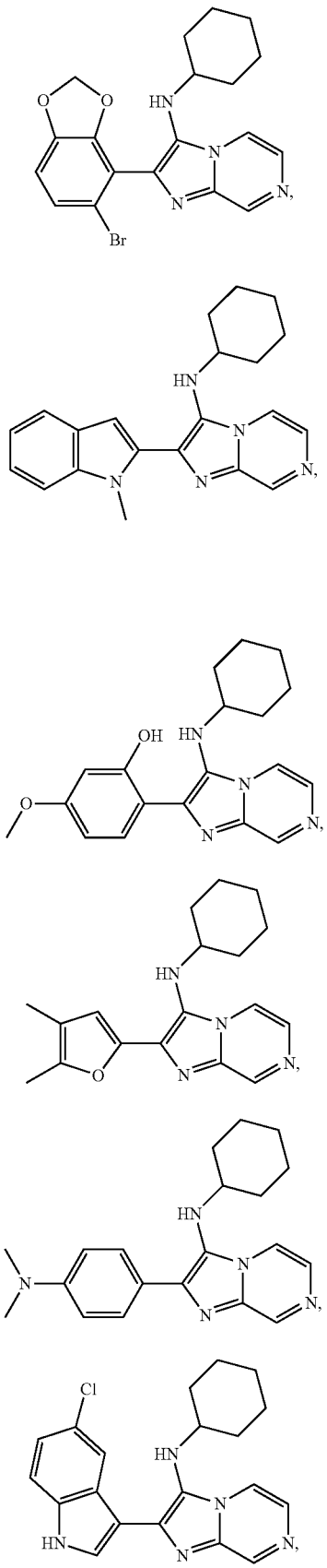
C6-Library 3
F5-Library 3
D6-Library 3
G5-Library 3
E6-Library 3
102
-continued
H5-Library 3
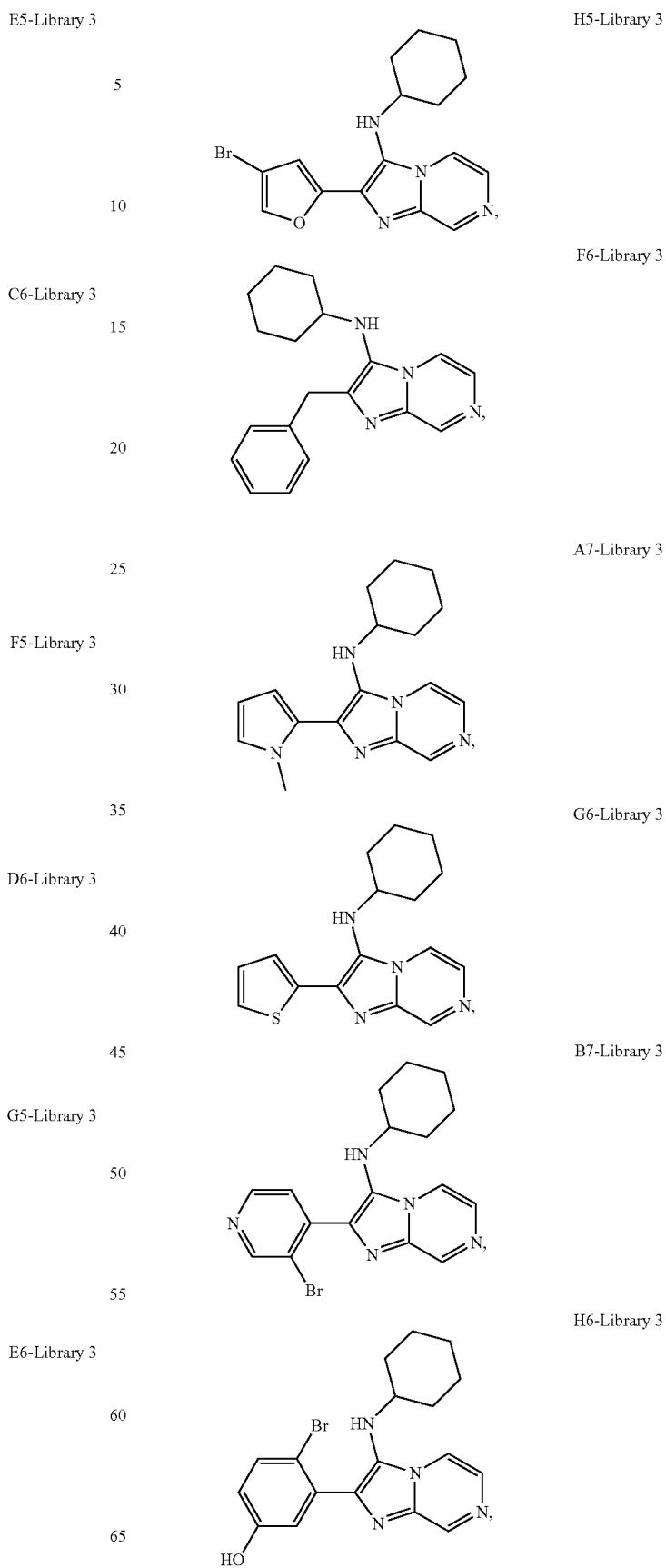
F6-Library 3
A7-Library 3
G6-Library 3
B7-Library 3
H6-Library 3

103
-continued
C7-Library 3
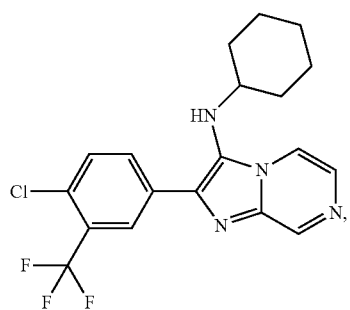
A8-Library 3
D7-Library 3
B8-Library 3
E7-Library 3
C8-Library 3
104
-continued
F7-Library 3
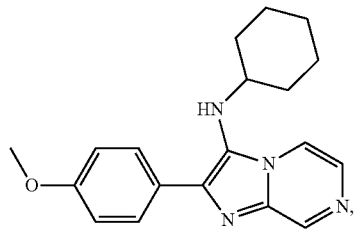
D8-Library 3
H7-Library 3
E8-Library 3
A9-Library 3
F8-Library 3

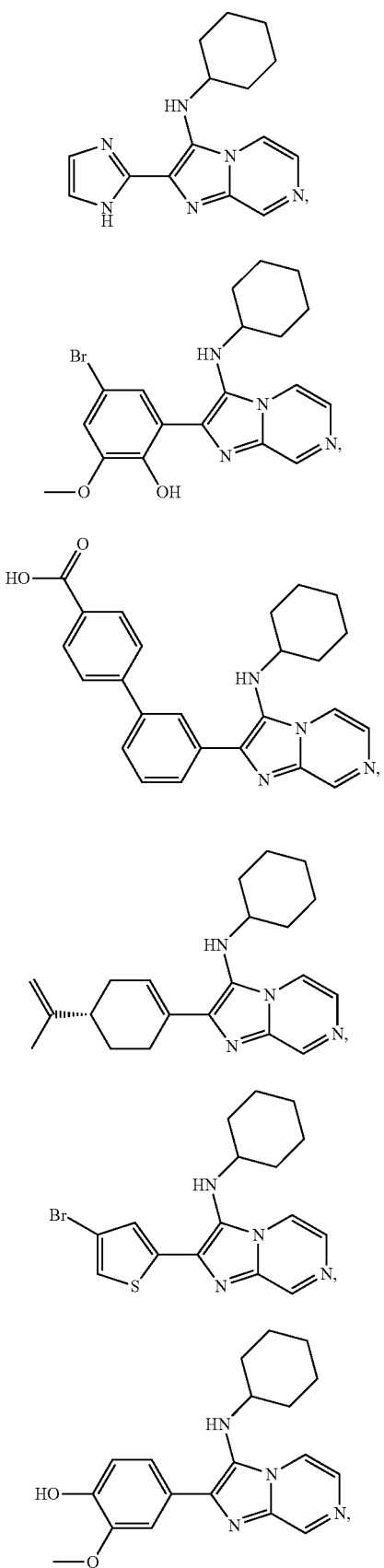
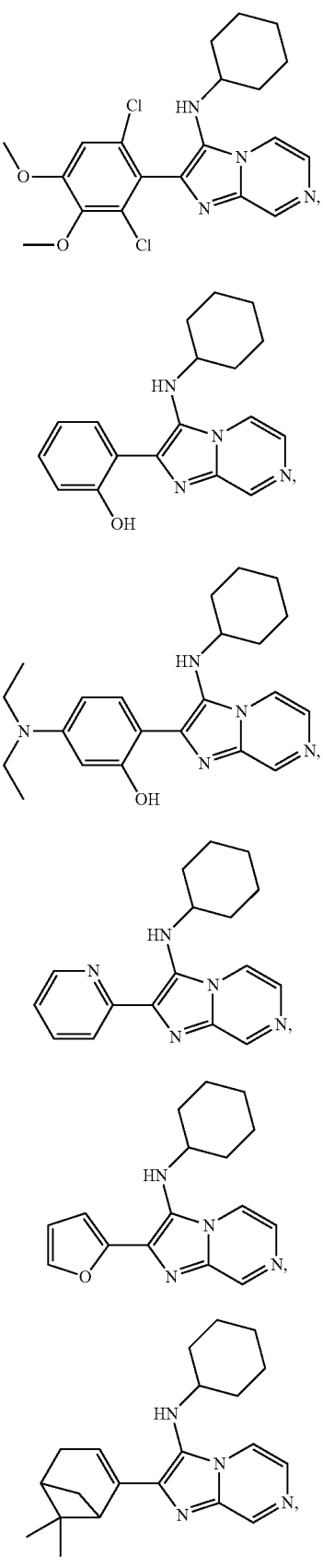

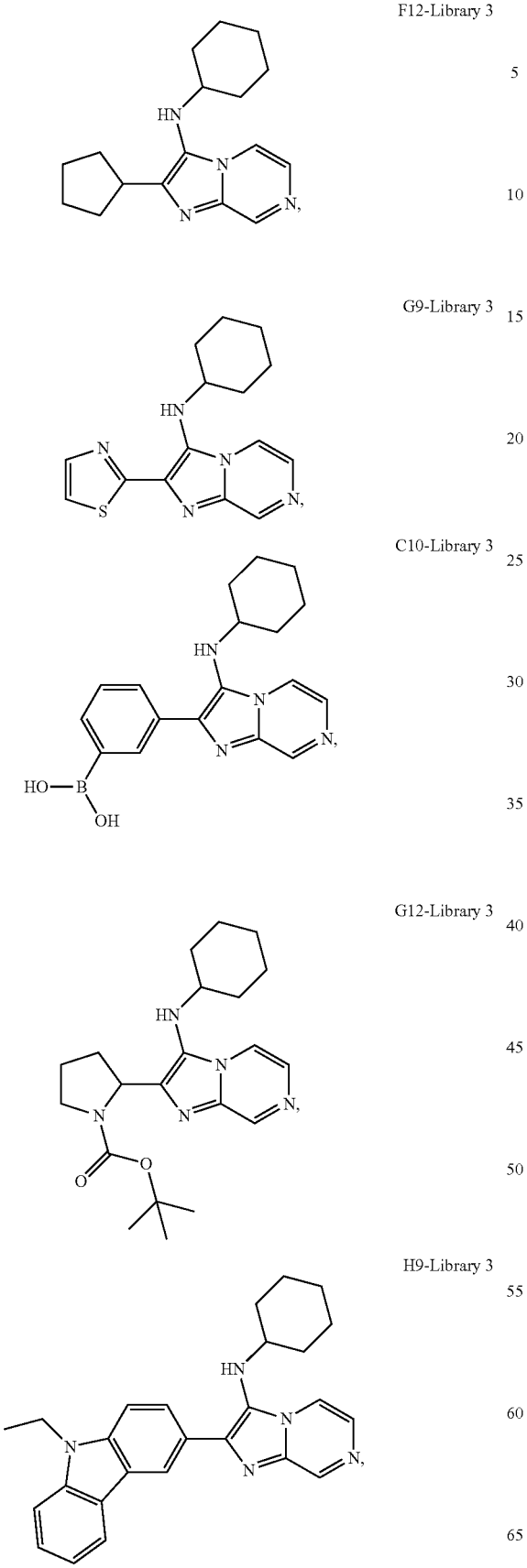
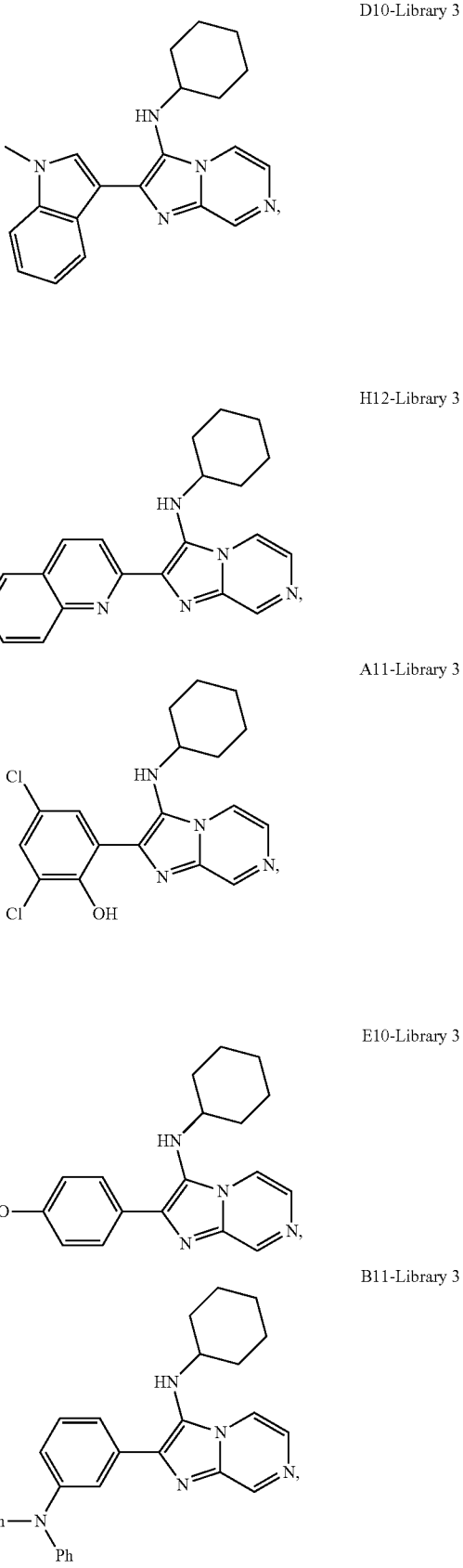

109 F10-Library 3
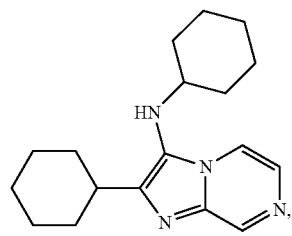
110 -continued E11-Library 3
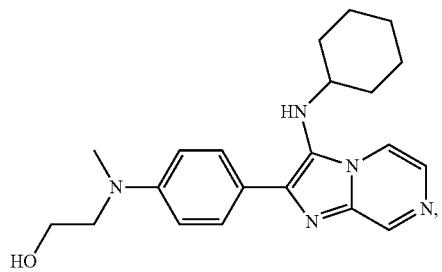
C11-Library 3
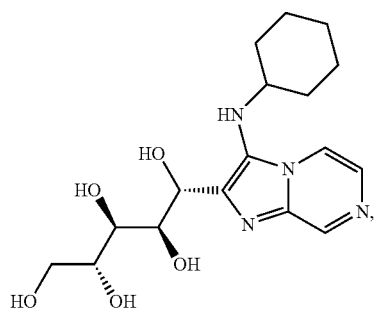
A12-Library 3
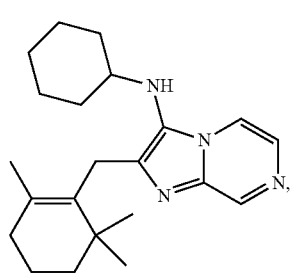
G10-Library 3
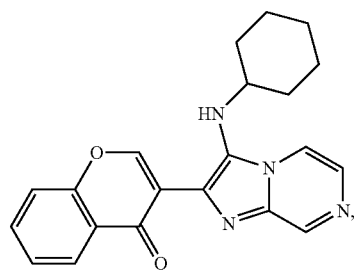
E1-Library 4
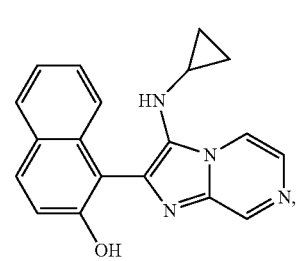
D11-Library 3
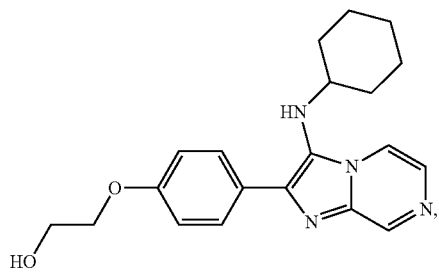
G11-Library 3
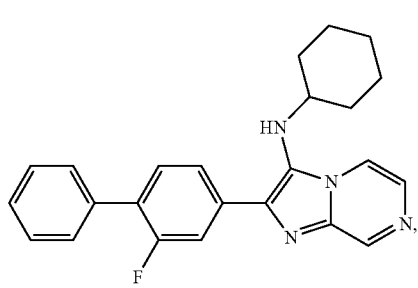
H10-Library 3
F1-Library 4
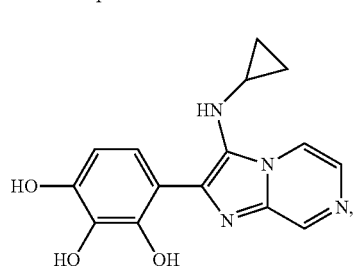

H11-Library 3
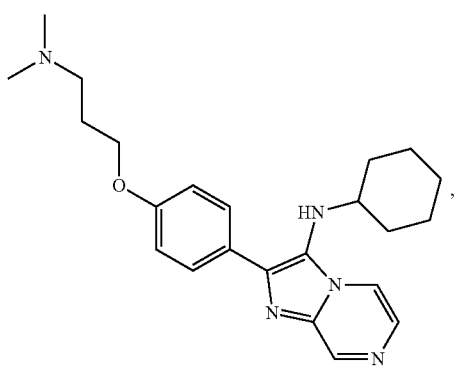
G1-Library 4
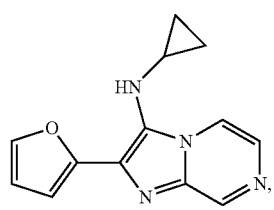
E12-Library 4
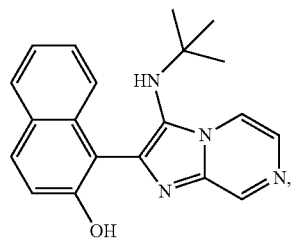
H1-Library 4
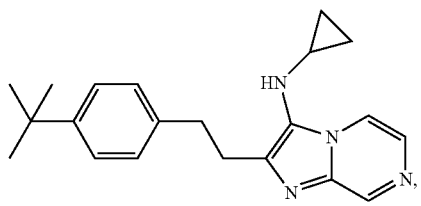
F12-Library 4
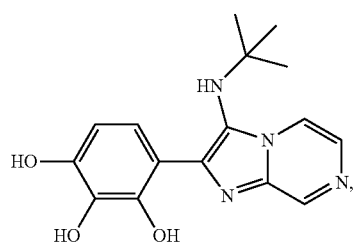
G12-Library 4
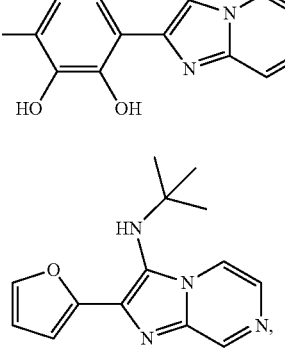
H12-Library 4
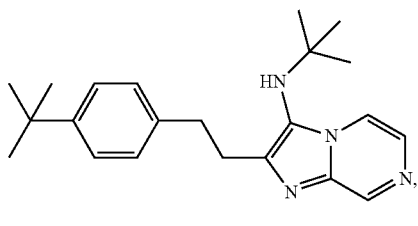
E2-Library 4
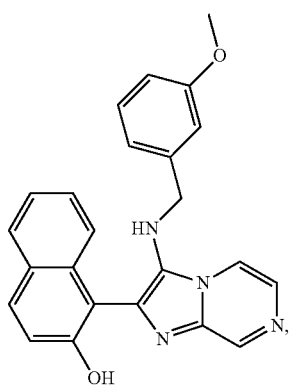
F2-Library 4
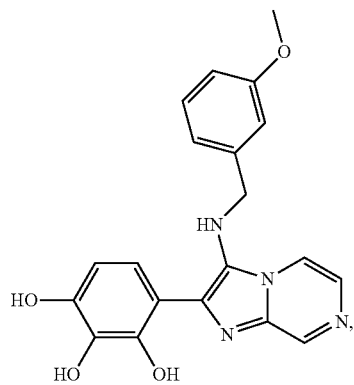
E3-Library 4
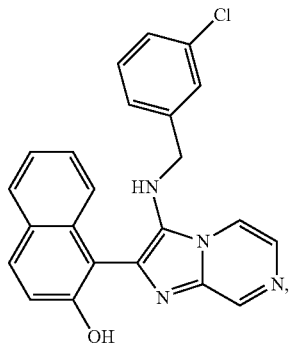

G2-Library 4
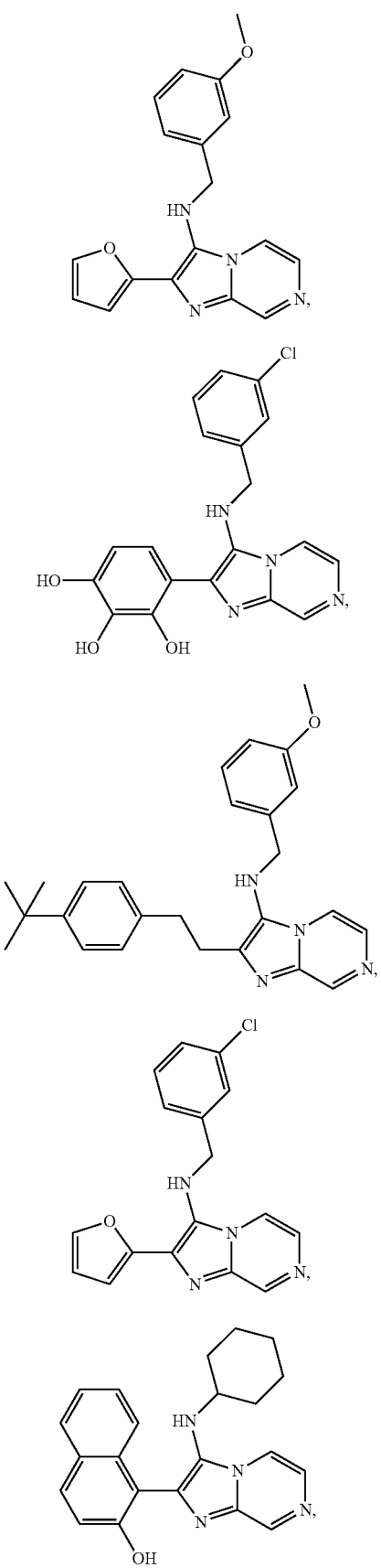
F3-Library 4
H2-Library 4
G3-Library 4
E10-Library 4
H3-Library 4
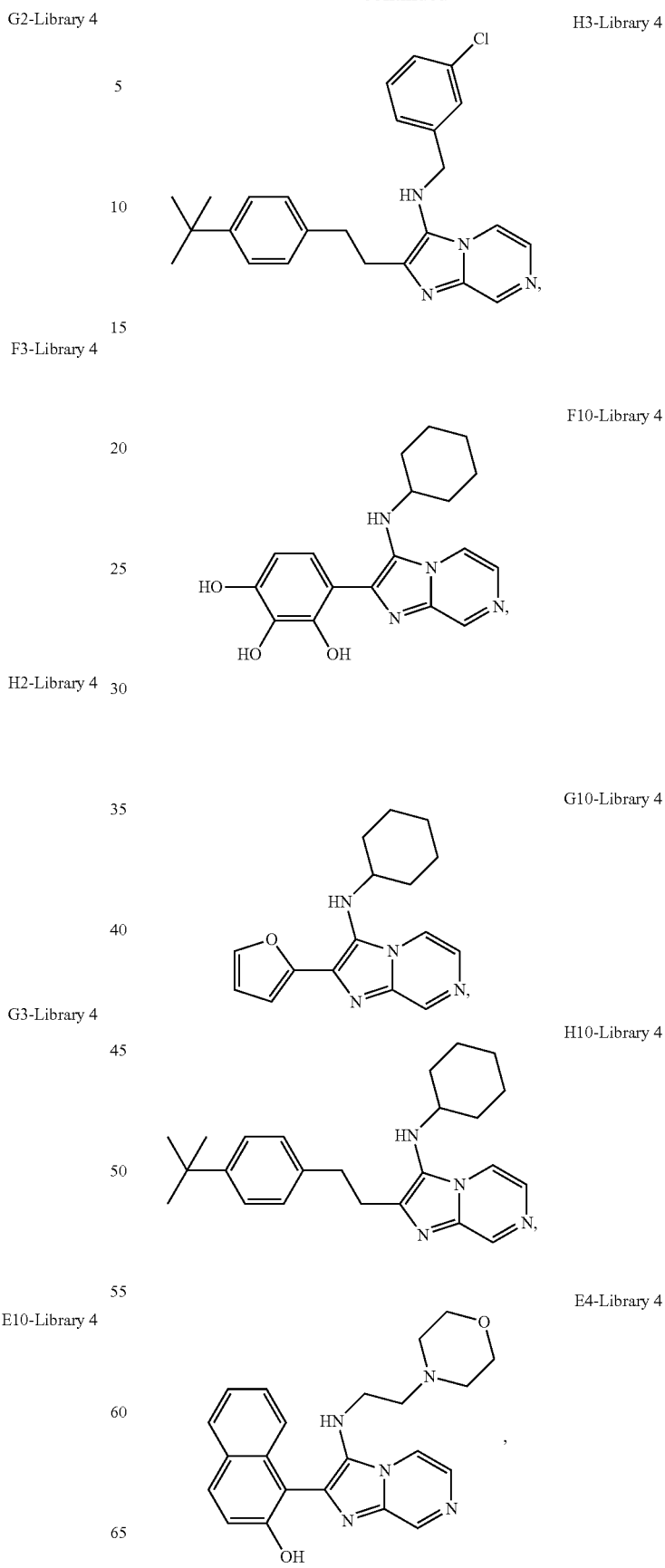
F10-Library 4
G10-Library 4
H10-Library 4
E4-Library 4

F4-Library 4
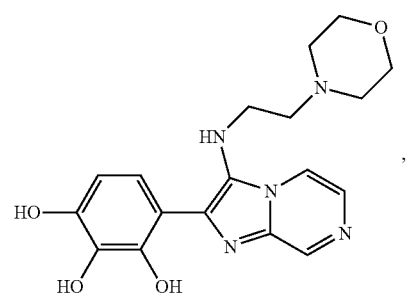
H4-Library 4
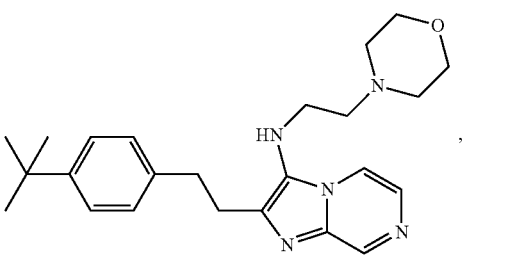
E5-Library 4
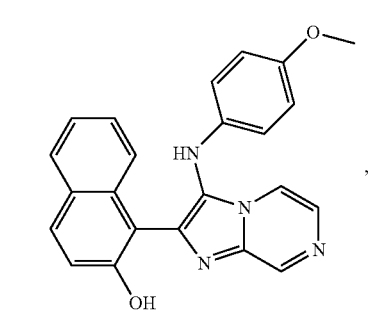
H9-Library 4
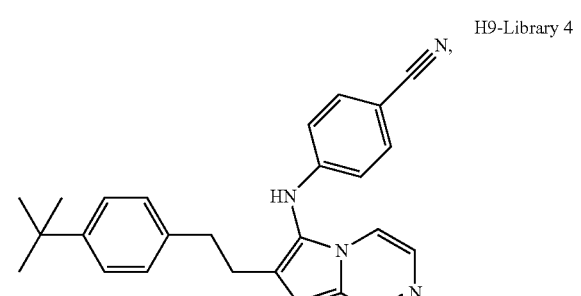
G4-Library 4
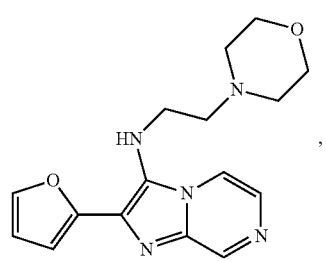
G5-Library 4
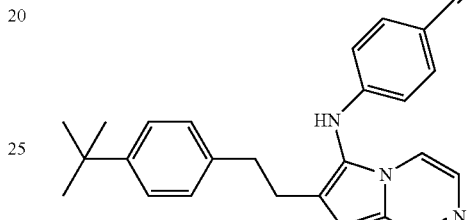
G9-Library 4
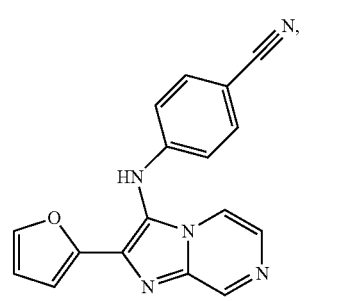
H5-Library 4
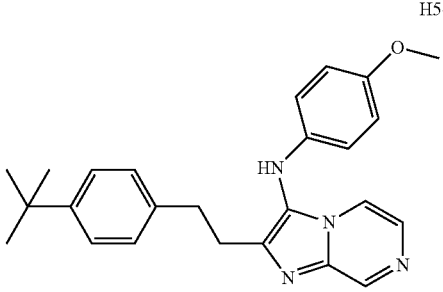
F5-Library 4
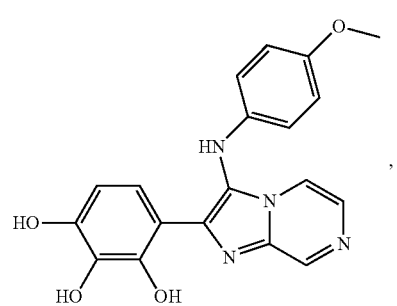
E6-Library 4
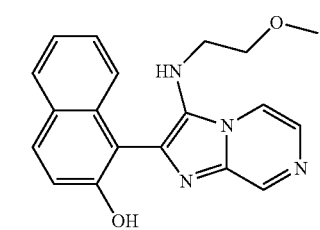

E11-Library 4
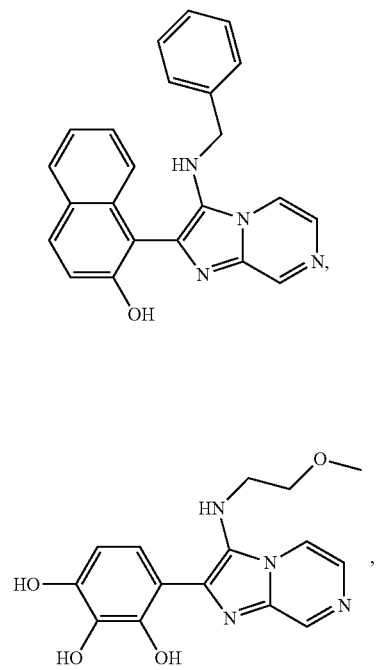
F6-Library 4
F11-Library 4
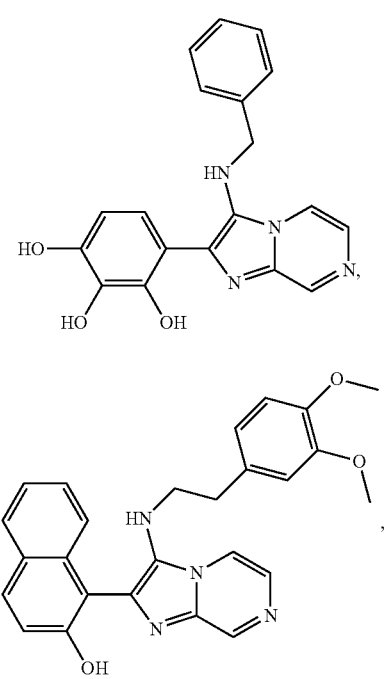
E7-Library 4
G6-Library 4
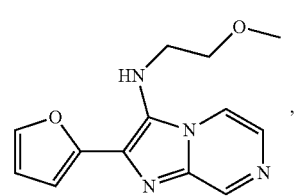
G11-Library 4
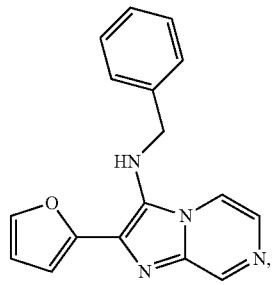
F7-Library 4
H6-Library 4
H11-Library 4
G7-Library 4

-continued

H7-Library 4

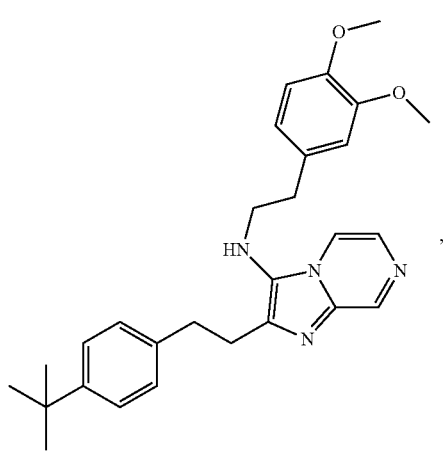

E9-Library 4

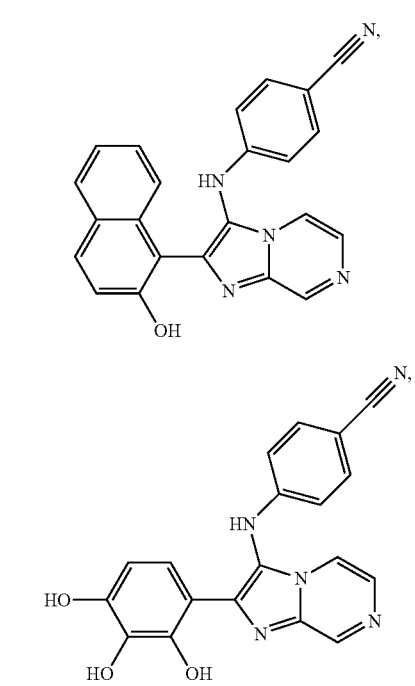

F9-Library 4

F8-Library 4

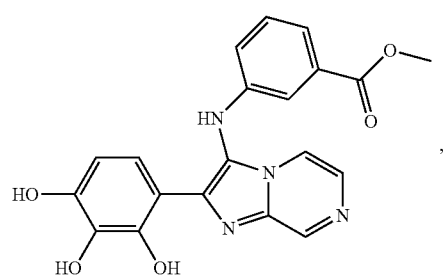

-continued

E8-Library 4

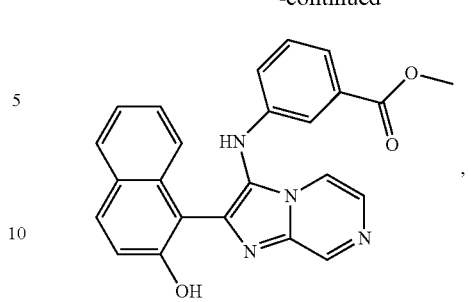

G8-Library 4

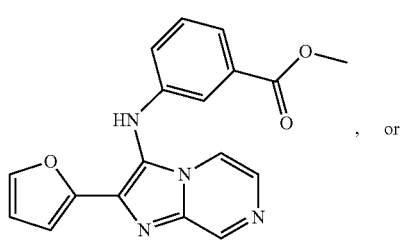, or

H8-Library 4

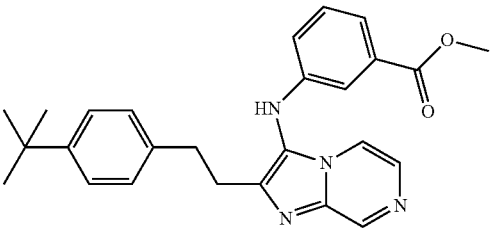, or a pharmaceutically acceptable salt thereof.

19. The method of claim 17, wherein the cancer is acute myeloid leukemia.

20. The method of claim 17, wherein the cancer is liver cancer.

21. The method of claim 17, wherein the cancer is lung cancer.

22. The method of claim 17, wherein the cancer is myelodysplastic syndrome (MDS).

* * * * *